US009758520B2

(12) United States Patent
Schwink et al.

(10) Patent No.: US 9,758,520 B2
(45) Date of Patent: Sep. 12, 2017

(54) SUBSTITUTED FUSED HETEROCYCLES AS GPR119 MODULATORS FOR THE TREATMENT OF DIABETES, OBESITY, DYSLIPIDEMIA AND RELATED DISORDERS

(71) Applicant: SANOFI, Paris (FR)

(72) Inventors: Lothar Schwink, Frankfurt am Main (DE); Christian Buning, Frankfurt am Main (DE); Heiner Glombik, Frankfurt am Main (DE); Matthias Gossel, Frankfurt am Main (DE); Dieter Kadereit, Frankfurt am Main (DE); Nis Halland, Frankfurt am Main (DE); Matthias Lohmann, Frankfurt am Main (DE); Christoph Pöverlein, Frankfurt am Main (DE); Kurt Ritter, Frankfurt am Main (DE)

(73) Assignee: SANOFI, Paris (FR)

( * ) Notice: Subject to any disclaimer, the term of this patent is extended or adjusted under 35 U.S.C. 154(b) by 0 days.

(21) Appl. No.: 15/284,213

(22) Filed: Oct. 3, 2016

(65) Prior Publication Data

US 2017/0022198 A1  Jan. 26, 2017

Related U.S. Application Data

(63) Continuation-in-part of application No. PCT/EP2015/057414, filed on Apr. 2, 2015.

(30) Foreign Application Priority Data

Apr. 4, 2014 (EP) .................................... 14305494

(51) Int. Cl.
| | | |
|---|---|---|
| *C07D 401/02* | (2006.01) | |
| *C07D 401/10* | (2006.01) | |
| *C07D 401/14* | (2006.01) | |
| *A61K 31/437* | (2006.01) | |
| *A61K 31/4353* | (2006.01) | |
| *C07D 471/04* | (2006.01) | |
| *C07D 231/56* | (2006.01) | |
| *C07D 249/18* | (2006.01) | |
| *A61K 45/06* | (2006.01) | |
| *A61K 31/4439* | (2006.01) | |
| *A61K 31/155* | (2006.01) | |
| *A61K 31/397* | (2006.01) | |
| *A61K 31/40* | (2006.01) | |
| *A61K 31/444* | (2006.01) | |
| *A61K 31/702* | (2006.01) | |

(52) U.S. Cl.
CPC .......... *C07D 471/04* (2013.01); *A61K 31/155* (2013.01); *A61K 31/397* (2013.01); *A61K 31/40* (2013.01); *A61K 31/444* (2013.01); *A61K 31/4439* (2013.01); *A61K 31/702* (2013.01); *A61K 45/06* (2013.01); *C07D 231/56* (2013.01); *C07D 249/18* (2013.01); *C07D 401/14* (2013.01)

(58) Field of Classification Search
CPC .. C07D 401/02; C07D 401/10; C07D 401/14; A61K 31/437; A61K 31/4353
USPC .......................... 546/119, 121; 514/300, 303
See application file for complete search history.

(56) References Cited

U.S. PATENT DOCUMENTS

2011/0306599 A1   12/2011   Inoue et al.

FOREIGN PATENT DOCUMENTS

| EP | 2387989 A2 | 11/2011 |
|---|---|---|
| WO | WO-2004/110994 A1 | 12/2004 |
| WO | WO-2007/124254 A2 | 11/2007 |
| WO | WO-2010/048149 A2 | 4/2010 |
| WO | WO-2010/048149 A3 | 4/2010 |
| WO | WO-2011/146335 A1 | 11/2011 |
| WO | WO-2012/037393 A1 | 3/2012 |
| WO | WO-2013/070463 A2 | 5/2013 |
| WO | WO-2013/070463 A3 | 5/2013 |
| WO | WO-2015/150564 A1 | 10/2015 |

OTHER PUBLICATIONS

ROTE LISTE®. (2011). Table of Contents (Machine Translation in English), one page.
ROTE LISTE®. (2014). Description of "Antiadipositic /Appetite Suppressant," in Rote Liste®, Chapter 6, two pages, (German Language).
ROTE LISTE®. (2014). Description of "Antidiabetics," in Rote Liste®, Chapter 12, eight pages, (German Language).
ROTE LISTE®. (2014). Description of "Antihypertensives," in Rote Liste®, Chapter 17, part A, ten pages, (German Language).
ROTE LISTE®. (2014). Description of "Antihypertensives," in Rote Liste®, Chapter 17, part B, nine pages, (German Language).
ROTE LISTE®. (2014). Description of "Diuretics," in Rote Liste®, Chapter 36, four pages, (German Language).
ROTE LISTE®. (2014). Description of "Lipid Countersink," in Rote Liste®, Chapter 58, six pages, (German Language).
USP Dictionary (2014) of USAN and International Drug Names, the United States Pharmacopeial Convention, 12601 Twinbrook Parkway, Rockville, MD 20852, three pages.

(Continued)

*Primary Examiner* — Niloofar Rahmani
(74) *Attorney, Agent, or Firm* — Morrison & Foerster LLP

(57) ABSTRACT

The present invention relates to substituted fused heterocyclic compounds.
The substituted fused heterocyclic compounds are GPR119 modulators and useful for the prevention and/or treatment of diabetes, obesity, dyslipidemia and related disorders. The invention furthermore relates to the use of substituted fused heterocyclic compounds as active ingredients in pharmaceuticals, and pharmaceutical compositions comprising them.

31 Claims, No Drawings

(56) References Cited

OTHER PUBLICATIONS

Tyle, P. (1986). "Iontophoretic Devices for Drug Delivery," *Pharmaceutical Research* 3(6):318-326.
International Search Report mailed Jun. 3, 2015 for International Application No. PCT/EP2015/057414 filed on Apr. 2, 2015, five pages.
U.S. Appl. No. 15/301,603, filed Oct. 3, 2016.
U.S. Appl. No. 15/284,334, filed Oct. 3, 2016.
Written Opinion of the International Searching Authority mailed Jun. 3, 2015 for International Application No. PCT/EP2015/057414 filed on Apr. 2, 2015, five pages.

SUBSTITUTED FUSED HETEROCYCLES AS GPR119 MODULATORS FOR THE TREATMENT OF DIABETES, OBESITY, DYSLIPIDEMIA AND RELATED DISORDERS

CROSS REFERENCE TO RELATED APPLICATIONS

This application is a continuation-in-part of International Application No. PCT/EP2015/057414, filed Apr. 2, 2015, which claims priority benefit to European Application No. 14305494.8, filed Apr. 4, 2014, the disclosures of each of which are herein incorporated by reference in their entirety.

The present invention relates to heterocyclic compounds of the formula I

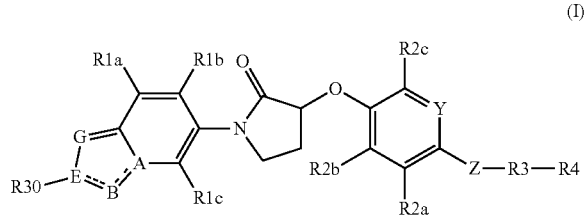

in which R1a, R1b, R1c, R2a, R2b, R2c, R3, R4, R30, A, B, E, G, Y and Z are defined as indicated below. The fused heterocyclic compounds I are GPR119 modulators and useful for the prevention and/or treatment of diabetes, obesity, dyslipidemia and related disorders. The invention furthermore relates to the use of fused heterocyic compounds of the formula I as active ingredients in pharmaceuticals, and pharmaceutical compositions comprising them.

GPR119 is a G-protein coupled receptor which is expressed predominantly in the beta cells of the pancreas and in the K- and L-cells of the intestine. In vitro studies have shown, that agonists of GPR119, via activation of the cAMP pathway in gut and pancreas derived cell lines, mediate the secretion of GLP-1 and insulin respectively. This supports the hypothesis, that modulators of GPR119, agonists in particular, may have utility to treat diabetes and related disorders by augmenting the secretion of insulin and intestinal hormones like GIP, GLP-1 and PYY. As the secretion of insulin was found to be strictly glucose-dependent, induction of hypoglycemic episodes may largely be avoided. Furthermore beneficial effects like reduced food intake may be expected from the release of intestinal peptides. Stimulation of the beta cell by activation of GPR119 may also improve beta cell function and beta cell mass. Studies of GPR119 agonists in rodents showed the predicted glucose lowering effects. For some such animal studies decreased food intake and weight loss was reported. Recently clinical trials with GPR119 agonists added evidence for a positive impact on lipid parameters i.e. elevation of HDL together with lowering of LDL and triglycerides in humans. WO2013/070463A2 discloses that GPR119 agonists may be used to treat abnormalities in blood lipids. In summary, modulators of GPR119, agonists in particular, may have therapeutic utility in the prevention and/or treatment of metabolic disorders in mammals and especially in humans. Examples of such disorders and diseases include type 2 diabetes mellitus, type 1 diabetes mellitus, impaired glucose tolerance, insulin resistance, loss of beta cell function, hyperglycemia, hypercholesterolemia, dyslipidemia, hypertriglyceridemia, syndrome X, metabolic syndrome, obesity, fatty liver, steatosis, steatohepatitis, cirrhosis, micro- and marcovascular disorders, high blood pressure, chronic low grade inflammation, retinopathy, neuropathy, nephropathy, atherosclerosis, coronary heart disease, endothelial dysfunction and bone-related diseases such as osteoporosis, rheumatoid arthritis or osteoarthritis.

Several modulators of GPR119 are known. For example WO2011146335 and WO2012037393 describe piperidinyl-substituted lactams as GPR119 modulators. WO2010048149 describes heterocyclic modulators of GPR119 for the treatment of disease and their preparation. WO2004110994 describes the preparation of piperazinyl-aryloxy and piperazinyl-heteroaryloxy-N-aryl lactams as 5-HT1B ligands.

It was an aim of the invention to provide novel compounds as active ingredients in pharmaceuticals.

It was another aim of the invention to provide novel compounds which will lower blood glucose in mammals and which are suitable for prevention and/or treatment of diabetes, obesity, dyslipidemia and related disorders.

A further aim was to provide novel GPR119 modulators, especially agonists, which can be used therapeutically for the prevention and/or treatment of diabetes, obesity, dyslipidemia and related disorders.

Accordingly a subject of the invention is a compound of the formula I

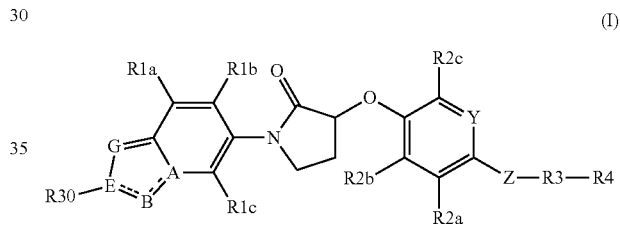

in which
A is N or C;
B is CO, N or CH;
E is N or C;
G is N or CR30;
  wherein at least one of the groups A, B, E or G is N;
R30 is H or $(CR11R12)_n$-R32;
R11, R12 are independently of each other H or $(C_1-C_6)$-alkyl;
n is 0, 1, 2 or 3;
R32 is $(C_1-C_6)$-alkyl, $(C_3-C_8)$-cycloalkyl, COOR13, CONR14R15, $SO_2$R16 or OH;
R13 is H or $(C_1-C_6)$-alkyl;
R14, R15 are independently of each other H, $(C_1-C_6)$-alkyl, $(C_1-C_6)$-alkyl substituted with OR17, or $(C_3-C_6)$-cycloalkyl;
  or R14 and R15 form together with the N-atom to which they are attached, a 4-, 5- or 6-membered heterocycle, optionally containing an additional heteroatom selected from the list O, S and NR18;
    wherein the 4-, 5- or 6-membered heterocycle may be optionally substituted with 1 to 3 groups selected from the list $(C_1-C_4)$-alkyl and OR17;
R16 is $(C_1-C_6)$-alkyl;
R17 is H or $(C_1-C_6)$-alkyl;
R18 is H or $(C_1-C_6)$-alkyl;
R1a, R1b, R1c are independently of each other H, F, Cl, Br, $(C_1-C_6)$-alkyl or ON;

R2a, R2b, R2c are independently of each other H, F, Cl, Br, $(C_1-C_6)$-alkyl or CN;
Y is N or CH;
Z is a bond, O, CR5R5', NR6, C=O, S, SO or $SO_2$;
R5, R5', R6 are independently of each other H or $(C_1-C_4)$-alkyl;
R3 is a bond or $(CR7R7')_p$;
p is 0, 1, 2, 3 or 4;
R7, R7' are independently of each other H or $(C_1-C_6)$-alkyl;
R4 is $(C_1-C_6)$-alkyl, OR8, $(C_3-C_8)$-cycloalkyl, $(C_5-C_8)$-bicycloalkyl, 4-, 5- or 6-membered heterocycle, phenyl or 5- or 6-membered heteroaryl ring;
   wherein the groups $(C_3-C_8)$-cycloalkyl, $(C_5-C_8)$-bicycloalkyl, 4-, 5- or 6-membered heterocycle, phenyl, 5- or 6-membered heteroaryl ring may be optionally substituted with 1 to 3 groups selected from $(C_1-C_4)$-alkyl, $(C_1-C_4)$-alkanoyl, hydroxy, hydroxy-$(C_1-C_4)$-alkyl, $(C_1-C_3)$-alkyloxy-$(C_1-C_4)$-alkyl, oxo, F or Cl;
R8 is H, $(C_1-C_6)$-alkyl, hydroxy-$(C_1-C_4)$-alkyl or $(C_1-C_3)$-alkyloxy-$(C_1-C_4)$-alkyl;
wherein at each occurrence the hydrogen atoms of alkyl groups may be partially or fully replaced by fluorine atoms; in any of its stereoisomeric forms, or a mixture of stereoisomeric forms in any ratio, or a physiologically acceptable salt thereof.

In another group of embodiments the 3-position of the central pyrrolidinone ring has (R)-configuration.

In another group of embodiments
A is N, B is CO, E is N and G is N.

In another group of embodiments
A is C, B is N, E is N and G is N.

In another group of embodiments
R11 and R12 are H.

In another group of embodiments
R32 is COOR13, CONR14R15 or OH.

In another group of embodiments
R32 is COOR13, CONR14R15.

In another group of embodiments
R32 is CONR14R15.

In another group of embodiments
R32 is $SO_2R16$.

In another group of embodiments
R14, R15 are independently of each other H, $(C_1-C_6)$-alkyl or $(C_1-C_6)$-alkyl) substituted with OR17.

In another group of embodiments
R16 is $CH_3$.

In another group of embodiments
R1a, R1c are independently of each other H, F or $CH_3$.

In another group of embodiments
R1b is H.

In another group of embodiments
R1a is H or F.

In another group of embodiments
R1b and R1c are H.

In another group of embodiments
R2a is H, F or $CH_3$.

In another group of embodiments
R2b and R2c are H.
Y is N.

In another group of embodiments
Z is O.

In another group of embodiments
Z is C=O.

In another group of embodiments
R7, R7' are H.

In another group of embodiments
p is 0, 1 or 2.

In another group of embodiments
R4 is $(C_1-C_6)$-alkyl, OR8, $(C_3-C_8)$-cycloalkyl or phenyl;
   wherein the groups $(C_3-C_8)$-cycloalkyl and phenyl may be optionally substituted with 1 to 3 groups F.

In another group of embodiments
R3 is a bond.

In another group of embodiments
R3 is $CH_2$ or $CH_2$—$CH_2$.

In another group of embodiments
R3 is $CH_2$.

In another group of embodiments
R4 is $(C_3-C_6)$-cycloalkyl.

In another group of embodiments the compound of the formula I is a compound of the formula Ia

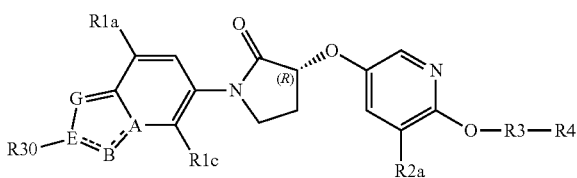

(Ia)

in which
A is N or C;
B is CO, N or CH;
E is N or C;
G is N or CR30;
   wherein at least one of the groups A, B, E or G is N;
R30 is H or $(CR11R12)_n$-R32;
R11, R12 are independently of each other H or $(C_1-C_6)$-alkyl;
n is 0, 1, 2 or 3;
R32 is $(C_1-C_6)$-alkyl, $(C_3-C_8)$-cycloalkyl, COOR13, CONR14R15, $SO_2R16$ or OH;
R13 is H or $(C_1-C_6)$-alkyl;
R14, R15 are independently of each other H, $(C_1-C_6)$-alkyl, $(C_1-C_6)$-alkyl substituted with OR17, or $(C_3-C_6)$-cycloalkyl;
   or R14 and R15 form together with the N-atom to which they are attached, a 4-, 5- or 6-membered heterocycle, optionally containing an additional heteroatom selected from the list O, S and NR18;
   wherein the 4-, 5- or 6-membered heterocycle may be optionally substituted with 1 to 3 groups selected from the list $(C_1-C_4)$-alkyl and OR17;
R16 is $(C_1-C_6)$-alkyl;
R17 is H or $(C_1-C_6)$-alkyl;
R18 is H or $(C_1-C_6)$-alkyl;
R1a, R1c are independently of each other H, F, Cl, Br, $(C_1-C_6)$-alkyl or CN;
R2a is H, F, Cl, Br, $(C_1-C_6)$-alkyl or CN;
R3 is a bond or $(CR7R7')_p$;
p is 0, 1, 2, 3 or 4;
R7, R7' are independently of each other H or $(C_1-C_6)$-alkyl;
R4 is $(C_1-C_6)$-alkyl, OR8, $(C_3-C_8)$-cycloalkyl, $(C_5-C_8)$-bicycloalkyl, 4-, 5- or 6-membered heterocycle, phenyl or 5- or 6-membered heteroaryl ring;
   wherein the groups $(C_3-C_8)$-cycloalkyl, $(C_5-C_8)$-bicycloalkyl, 4-, 5- or 6-membered heterocycle, phenyl, 5- or 6-membered heteroaryl ring may be optionally substituted with 1 to 3 groups selected from $(C_1-C_4)$-alkyl, $(C_1-C_4)$-alkanoyl, hydroxy, hydroxy-$(C_1-C_4)$-alkyl, $(C_1-C_3)$-alkyloxy-$(C_1-C_4)$-alkyl, oxo, F or Cl;

R8 is H, $(C_1-C_6)$-alkyl, hydroxy-$(C_1-C_4)$-alkyl or $(C_1-C_3)$-alkyloxy-$(C_1-C_4)$-alkyl;

wherein at each occurrence the hydrogen atoms of alkyl groups may be partially or fully replaced by fluorine atoms; in any of its stereoisomeric forms, or a mixture of stereoisomeric forms in any ratio, or a physiologically acceptable salt thereof.

In another group of embodiments the compound of the formula I is a compound of the formula Ia, in which A is N or C;
B is CO, N or CH;
E is N or C;
G is N or CR30;
  wherein at least one of the groups A, B, E or G is N;
R30 is $(CR11R12)_n$-R32;
R11, R12 are independently of each other H or $(C_1-C_6)$-alkyl;
n is 0, 1 or 2;
R32 is $(C_1-C_6)$-alkyl, $(C_3-C_8)$-cycloalkyl, COOR13, CONR14R15 or OH;
R13 is H or $(C_1-C_6)$-alkyl;
R14, R15 are independently of each other H, $(C_1-C_6)$-alkyl, $(C_1-C_6)$-alkyl substituted with OR17, or $(C_3-C_6)$-cycloalkyl;
  or R14 and R15 form together with the N-atom to which they are attached, a 4-, 5- or 6-membered heterocycle, optionally containing an additional heteroatom selected from the list O, S and NR18;
    wherein the 4-, 5- or 6-membered heterocycle may be optionally substituted with 1 to 3 groups selected from the list $(C_1-C_4)$-alkyl and OR17;
R16 is $(C_1-C_6)$-alkyl;
R17 is H or $(C_1-C_6)$-alkyl;
R18 is H or $(C_1-C_6)$-alkyl;
R1a, R1c are independently of each other H, F, Cl, Br, $(C_1-C_6)$-alkyl or CN;
R2a is H, F, Cl, Br, $(C_1-C_6)$-alkyl or CN;
R3 is $CH_2$;
R4 is $(C_3-C_8)$-cycloalkyl which may be optionally substituted with 1 to 3 groups selected from $(C_1-C_4)$-alkyl and F;

wherein at each occurrence the hydrogen atoms of alkyl groups may be partially or fully replaced by fluorine atoms; in any of its stereoisomeric forms, or a mixture of stereoisomeric forms in any ratio, or a physiologically acceptable salt thereof.

In another group of embodiments the compound of the formula I is a compound of the formula Ia, in which A is N or C;
B is CO, N or CH;
E is N or C;
G is N or CR30;
wherein at least one of the groups A, B, E or G is N;
R30 is $(CR11R12)_n$-R32;
R11, R12 are independently of each other H or $(C_1-C_6)$-alkyl;
n is 0, 1 or 2;
R32 is $(C_1-C_6)$-alkyl, $(C_3-C_8)$-cycloalkyl, COOR13, CONR14R15 or OH;
R13 is H or $(C_1-C_6)$-alkyl;
R14, R15 are independently of each other H, $(C_1-C_6)$-alkyl, $(C_1-C_6)$-alkyl substituted with OR17, or $(C_3-C_6)$-cycloalkyl;
  or R14 and R15 form together with the N-atom to which they are attached, a 4-, 5- or 6-membered heterocycle, optionally containing an additional heteroatom selected from the list O, S and NR18;
    wherein the 4-, 5- or 6-membered heterocycle may be optionally substituted with 1 to 3 groups selected from the list $(C_1-C_4)$-alkyl and OR17;
R16 is $(C_1-C_6)$-alkyl;
R17 is H or $(C_1-C_6)$-alkyl;
R18 is H or $(C_1-C_6)$-alkyl;
R1a, R1c are independently of each other H, F, Cl, Br, $(C_1-C_6)$-alkyl or CN;
R2a is H, F, Cl, Br, $(C_1-C_6)$-alkyl or CN;
R3 is $CH_2$;
R4 $(C_3-C_8)$-cycloalkyl;

wherein at each occurrence the hydrogen atoms of alkyl groups may be partially or fully replaced by fluorine atoms; in any of its stereoisomeric forms, or a mixture of stereoisomeric forms in any ratio, or a physiologically acceptable salt thereof.

In another group of embodiments the compound of the formula I is a compound of the formula Ia, in which A is N or C;
B is CO, N or CH;
E is N or C;
G is N or CR30;
wherein at least one of the groups A, B, E or G is N;
R30 is $CH_2CONR14R15$;
R14, R15 are independently of each other H, $(C_1-C_6)$-alkyl, $(C_1-C_6)$-alkyl substituted with OR17, or $(C_3-C_6)$-cycloalkyl;
R17 is H or $(C_1-C_6)$-alkyl;
R1a, R1c are independently of each other H or F;
R2a is H;
R3 is $CH_2$;
R4 $(C_3-C_8)$-cycloalkyl;
in any of its stereoisomeric forms, or a mixture of stereoisomeric forms in any ratio, or a physiologically acceptable salt thereof.

The dotted lines between E and B or B and A in formulas I and Ia indicate that in theses positions a double bond may be present depending on the definitions of E, B and A (see for example Example 1-01 for the sequence C=N—N, Example 1-03 for the sequence C=C—N, Example 1-04 for the sequence N—CO—N, Example 1-05 for the sequence N=C—N and Example 1-15 for the sequence N—N=C).

In case that E and B are connected by a double bond and E is N, no group R30 is present in formula I, Ia or Ib.

In another group of embodiments the compound of the formula I is a compound of the formula Ib (Ib)

in which
B is CO, N or CH;
E is N or C;
G is N or CR30;
  wherein at least one of the groups B, E or G is N;
R30 is H or $(CR11R12)_n$-R32;
R11, R12 are independently of each other H or $(C_1-C_6)$-alkyl;

n is 0, 1, 2 or 3;
R32 is $(C_1-C_6)$-alkyl, $(C_3-C_8)$-cycloalkyl, COOR13, CONR14R15, SO$_2$R16 or OH;
R13 is H or $(C_1-C_6)$-alkyl;
R14, R15 are independently of each other H, $(C_1-C_6)$-alkyl, $(C_1-C_6)$-alkyl substituted with OR17, or $(C_3-C_6)$-cycloalkyl;
  or R14 and R15 form together with the N-atom to which they are attached, a 4-, 5- or 6-membered heterocycle, optionally containing an additional heteroatom selected from the list O, S and NR18;
    wherein the 4-, 5- or 6-membered heterocycle may be optionally substituted with 1 to 3 groups selected from the list $(C_1-C_4)$-alkyl and OR17;
R16 is $(C_1-C_6)$-alkyl;
R17 is H or $(C_1-C_6)$-alkyl;
R18 is H or $(C_1-C_6)$-alkyl;
R1a, R1c are independently of each other H, F, Cl, Br, $(C_1-C_6)$-alkyl or CN;
R2a is H, F, Cl, Br, $(C_1-C_6)$-alkyl or CN;
R3 is a bond or $(CR7R7')_p$;
p is 0, 1, 2, 3 or 4;
R7, R7' are independently of each other H or $(C_1-C_6)$-alkyl;
R4 is $(C_1-C_6)$-alkyl, OR8, $(C_3-C_8)$-cycloalkyl, $(C_5-C_8)$-bicycloalkyl, 4-, 5- or 6-membered heterocycle, phenyl or 5- or 6-membered heteroaryl ring;
  wherein the groups $(C_3-C_8)$-cycloalkyl, $(C_5-C_8)$-bicycloalkyl, 4-, 5- or 6-membered heterocycle, phenyl, 5- or 6-membered heteroaryl ring may be optionally substituted with 1 to 3 groups selected from $(C_1-C_4)$-alkyl, $(C_1-C_4)$-alkanoyl, hydroxy-, hydroxy-$(C_1-C_4)$-alkyl-, $(C_1-C_3)$-alkyloxy-$(C_1-C_4)$-alkyl, oxo, F or Cl;
R8 is H, $(C_1-C_6)$-alkyl, hydroxy-$(C_1-C_4)$-alkyl or $(C_1-C_3)$-alkyloxy-$(C_1-C_4)$-alkyl;
wherein at each occurrence the hydrogen atoms of alkyl groups may be partially or fully replaced by fluorine atoms;
in any of its stereoisomeric forms, or a mixture of stereoisomeric forms in any ratio, or a physiologically acceptable salt thereof.

In another group of embodiments the compound of the formula I is a compound of the formula Ib, in which
R30 is $(CR11R12)_n$-R32;
R11, R12 are independently of each other H or $(C_1-C_6)$-alkyl;
n is 1;
R32 is CONR14R15;
R14, R15 are independently of each other H, $(C_1-C_6)$-alkyl, $(C_1-C_6)$-alkyl substituted with OR17, or $(C_3-C_6)$-cycloalkyl;
  or R14 and R15 form together with the N-atom to which they are attached, a 4-, 5- or 6-membered heterocycle, optionally containing an additional heteroatom selected from the list O, S and NR18;
    wherein the 4-, 5- or 6-membered heterocycle may be optionally substituted with 1 to 3 groups selected from the list $(C_1-C_4)$-alkyl and OR17;
R17 is H or $(C_1-C_6)$-alkyl;
R18 is H or $(C_1-C_6)$-alkyl;
R1a, R1c are independently of each other H, F, Cl, Br, $(C_1-C_6)$-alkyl or CN;
R2a is H, F, Cl, Br, $(C_1-C_6)$-alkyl or CN;
R3 is CH$_2$;
R4 $(C_3-C_8)$-cycloalkyl;
wherein at each occurrence the hydrogen atoms of alkyl groups may be partially or fully replaced by fluorine atoms;
in any of its stereoisomeric forms, or a mixture of stereoisomeric forms in any ratio, or a physiologically acceptable salt thereof.

In another group of embodiments the compound of the formula I is a compound of the formula Ib, in which
B is CO, N or CH;
E is N or C;
G is N or CR30;
  wherein at least two of the groups B, E or G are N.

In another group of embodiments the compound of the formula I is a compound of the formula Ic

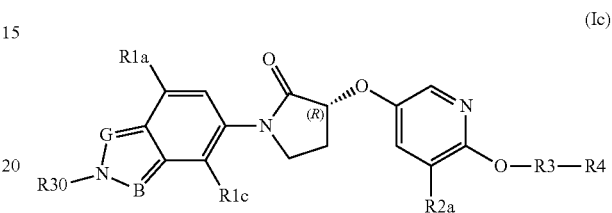

in which
B is N or CH;
G is N or CR30;
  wherein at least one of the groups B or G is N;
R30 is H or $(CR11R12)_n$-R32;
R11, R12 are independently of each other H or $(C_1-C_6)$-alkyl;
n is 0, 1, 2 or 3;
R32 is $(C_1-C_6)$-alkyl, $(C_3-C_8)$-cycloalkyl, COOR13, CONR14R15, SO$_2$R16 or OH;
R13 is H or $(C_1-C_6)$-alkyl;
R14, R15 are independently of each other H, $(C_1-C_6)$-alkyl, $(C_1-C_6)$-alkyl substituted with OR17, or $(C_3-C_6)$-cycloalkyl;
  or R14 and R15 form together with the N-atom to which they are attached, a 4-, 5- or 6-membered heterocycle, optionally containing an additional heteroatom selected from the list O, S and NR18;
    wherein the 4-, 5- or 6-membered heterocycle may be optionally substituted with 1 to 3 groups selected from the list $(C_1-C_4)$-alkyl and OR17;
R16 is $(C_1-C_6)$-alkyl;
R17 is H or $(C_1-C_6)$-alkyl;
R18 is H or $(C_1-C_6)$-alkyl;
R1a, R1c are independently of each other H, F, Cl, Br, $(C_1-C_6)$-alkyl or CN;
R2a is H, F, Cl, Br, $(C_1-C_6)$-alkyl or CN;
R3 is a bond or $(CR7R7')_p$;
p is 0, 1, 2, 3 or 4;
R7, R7' are independently of each other H or $(C_1-C_6)$-alkyl;
R4 is $(C_1-C_6)$-alkyl, OR8, $(C_3-C_8)$-cycloalkyl, $(C_5-C_8)$-bicycloalkyl, 4-, 5- or 6-membered heterocycle, phenyl or 5- or 6-membered heteroaryl ring;
  wherein the groups $(C_3-C_8)$-cycloalkyl, $(C_5-C_8)$-bicycloalkyl, 4-, 5- or 6-membered heterocycle, phenyl, 5- or 6-membered heteroaryl ring may be optionally substituted with 1 to 3 groups selected from $(C_1-C_4)$-alkyl, $(C_1-C_4)$-alkanoyl, hydroxy, hydroxy-$(C_1-C_4)$-alkyl, $(C_1-C_3)$-alkyloxy-$(C_1-C_4)$-alkyl, oxo, F or Cl;
R8 is H, $(C_1-C_6)$-alkyl, hydroxy-$(C_1-C_4)$-alkyl or $(C_1-C_3)$-alkyloxy-$(C_1-C_4)$-alkyl;
wherein at each occurrence the hydrogen atoms of alkyl groups may be partially or fully replaced by fluorine atoms;

in any of its stereoisomeric forms, or a mixture of stereoisomeric forms in any ratio, or a physiologically acceptable salt thereof.

In another group of embodiments the compound of the formula I is a compound of the formula Ic, in which
R30 is CH$_2$CONR14R15;
R14, R15 are independently of each other H, (C$_1$-C$_6$)-alkyl, (C$_1$-C$_6$)-alkyl substituted with OR17, or (C$_3$-C$_6$)-cycloalkyl;
R17 is H or (C$_1$-C$_6$)-alkyl;
R1a, R1c are independently of each other H or F;
R2a is H;
R3 is CH$_2$;
R4 (C$_3$-C$_8$)-cycloalkyl;
in any of its stereoisomeric forms, or a mixture of stereoisomeric forms in any ratio, or a physiologically acceptable salt thereof.

In another group of embodiments the compound of the formula I is a compound of the formula Id (Id)

in which
R30 is H or (CR11R12)$_n$-R32;
R11, R12 are independently of each other H or (C$_1$-C$_6$)-alkyl;
n is 0, 1, 2 or 3;
R32 is (C$_1$-C$_6$)-alkyl, (C$_3$-C$_8$)-cycloalkyl, COOR13, CONR14R15, SO$_2$R16 or OH;
R13 is H or (C$_1$-C$_6$)-alkyl;
R14, R15 are independently of each other H, (C$_1$-C$_6$)-alkyl, (C$_1$-C$_6$)-alkyl substituted with OR17, or (C$_3$-C$_6$)-cycloalkyl;
or R14 and R15 form together with the N-atom to which they are attached, a 4-, 5- or 6-membered heterocycle, optionally containing an additional heteroatom selected from the list O, S and NR18;
wherein the 4-, 5- or 6-membered heterocycle may be optionally substituted with 1 to 3 groups selected from the list (C$_1$-C$_4$)-alkyl and OR17;
R16 is (C$_1$-C$_6$)-alkyl;
R17 is H or (C$_1$-C$_6$)-alkyl;
R18 is H or (C$_1$-C$_6$)-alkyl;
R1a, R1c are independently of each other H, F, Cl, Br, (C$_1$-C$_6$)-alkyl or CN;
R2a is H, F, Cl, Br, (C$_1$-C$_6$)-alkyl or CN;
R3 is a bond or (CR7R7')$_p$;
p is 0, 1, 2, 3 or 4;
R7, R7' are independently of each other H or (C$_1$-C$_6$)-alkyl;
R4 is (C$_1$-C$_6$)-alkyl, OR8, (C$_3$-C$_8$)-cycloalkyl, (C$_5$-C$_8$)-bicycloalkyl, 4-, 5- or 6-membered heterocycle, phenyl or 5- or 6-membered heteroaryl ring;
wherein the groups (C$_3$-C$_8$)-cycloalkyl, (C$_5$-C$_8$)-bicycloalkyl, 4-, 5- or 6-membered heterocycle, phenyl, 5- or 6-membered heteroaryl ring may be optionally substituted with 1 to 3 groups selected from (C$_1$-C$_4$)-alkyl, (C$_1$-C$_4$)-alkanoyl, hydroxy-, hydroxy-(C$_1$-C$_4$)-alkyl-, (C$_1$-C$_3$)-alkyloxy-(C$_1$-C$_4$)-alkyl, oxo, F or Cl;
R8 is H, (C$_1$-C$_6$)-alkyl, hydroxy-(C$_1$-C$_4$)-alkyl or (C$_1$-C$_3$)-alkyloxy-(C$_1$-C$_4$)-alkyl;
wherein at each occurrence the hydrogen atoms of alkyl groups may be partially or fully replaced by fluorine atoms;
in any of its stereoisomeric forms, or a mixture of stereoisomeric forms in any ratio, or a physiologically acceptable salt thereof.

In another group of embodiments the compound of the formula I is a compound of the formula Id, in which
R30 is CH$_2$CONR14R15;
R14, R15 are independently of each other H, (C$_1$-C$_6$)-alkyl, (C$_1$-C$_6$)-alkyl substituted with OR17, or (C$_3$-C$_6$)-cycloalkyl;
R17 is H or (C$_1$-C$_6$)-alkyl;
R1a, R1c are independently of each other H or F;
R2a is H;
R3 is CH$_2$;
R4 (C$_3$-C$_8$)-cycloalkyl;
in any of its stereoisomeric forms, or a mixture of stereoisomeric forms in any ratio, or a physiologically acceptable salt thereof.

In another embodiment compounds of the formula I are encompassed selected from Examples 1-01 to 1-34 and 2-01 to 2-05.

In another embodiment compounds of the formula I are encompassed selected from the following list:
(3R)-3-[[6-(Cyclopropylmethoxy)-3-pyridyl]oxy]-1-(2-cyclopropyl-[1,2,4]triazolo[1,5-a]pyridin-6-yl)pyrrolidin-2-one,
(3R)-3-[[6-(cyclopropylmethoxy)-3-pyridyl]oxy]-1-([1,2,4]triazolo[1,5-a]pyridin-6-yl)pyrrolidin-2-one,
(3R)-3-[[6-(cyclopropylmethoxy)-3-pyridyl]oxy]-1-imidazo[1,2-a]pyridin-6-yl-pyrrolidin-2-one,
methyl 2-[6-[(3R)-3-[[6-(cyclopropylmethoxy)-3-pyridyl]oxy]-2-oxo-pyrrolidin-1-yl]-1-methyl-3-oxo-imidazo[1,5-a]pyridin-2-yl]acetate,
(3R)-3-[[6-(cyclopropylmethoxy)-3-pyridyl]oxy]-1-([1,2,4]triazolo[4,3-a]pyridin-6-yl)pyrrolidin-2-one,
2-[6-[(3R)-3-[[6-(cyclopropylmethoxy)-3-pyridyl]oxy]-2-oxo-pyrrolidin-1-yl]-[1,2,4]triazolo[1,5-a]pyridin-2-yl]acetic acid,
methyl 2-[6-[(3R)-3-[[6-(cyclopropylmethoxy)-3-pyridyl]oxy]-2-oxo-pyrrolidin-1-yl]-[1,2,4]triazolo[1,5-a]pyridin-2-yl]acetate,
methyl 6-[(3R)-3-[[6-(cyclopropylmethoxy)-3-pyridyl]oxy]-2-oxo-pyrrolidin-1-yl]-[1,2,4]triazolo[1,5-a]pyridine-2-carboxylate,
2-[6-[(3R)-3-[[6-(cyclopropylmethoxy)-3-pyridyl]oxy]-2-oxo-pyrrolidin-1-yl]-3-oxo-[1,2,4]triazolo[4,3-a]pyridin-2-yl]-N,N-dimethyl-acetamide,
8-fluoro-6-[(3R)-3-[[6-(4-fluorophenoxy)-3-pyridyl]oxy]-2-oxo-pyrrolidin-1-yl]-2H-[1,2,4]triazolo[4,3-a]pyridin-3-one,
2-[6-[(3R)-3-[[6-(4-fluorophenoxy)-3-pyridyl]oxy]-2-oxo-pyrrolidin-1-yl]-3-oxo-[1,2,4]triazolo[4,3-a]pyridin-2-yl]-N,N-dimethyl-acetamide,
2-[6-[(3R)-3-[4-(2-cyclopropylacetyl)phenoxy]-2-oxo-pyrrolidin-1-yl]-3-oxo-[1,2,4]triazolo[4,3-a]pyridin-2-yl]-N,N-dimethyl-acetamide,
2-[6-[(3R)-3-[4-(2-cyclopropylacetyl)phenoxy]-2-oxo-pyrrolidin-1-yl]-8-fluoro-3-oxo-[1,2,4]triazolo[4,3-a]pyridin-2-yl]-N,N-dimethyl-acetamide,
6-[(3R)-3-[[6-(cyclopropylmethoxy)-3-pyridyl]oxy]-2-oxo-pyrrolidin-1-yl]-2H-[1,2,4]triazolo[4,3-a]pyridin-3-one, methyl 2-[6-[(3R)-3-[[6-(cyclopropylmethoxy)-3-pyridyl]oxy]-2-oxo-pyrrolidin-1-yl]indazol-2-yl]acetate,
2-[6-[(3R)-3-[[6-(cyclopropylmethoxy)-3-pyridyl]oxy]-2-oxo-pyrrolidin-1-yl]indazol-2-yl]acetic acid,
2-[5-[(3R)-3-[[6-(cyclopropylmethoxy)-3-pyridyl]oxy]-2-oxo-pyrrolidin-1-yl]benzotriazol-2-yl]acetic acid,
methyl 2-[5-[(3R)-3-[[6-(cyclopropylmethoxy)-3-pyridyl]oxy]-2-oxo-pyrrolidin-1-yl]benzotriazol-2-yl]acetate,
2-[6-[(3R)-3-[[6-(cyclopropylmethoxy)-3-pyridyl]oxy]-2-oxo-pyrrolidin-1-yl]imidazo[1,2-a]pyridin-2-yl]acetic acid,
methyl 2-[6-[(3R)-3-[[6-(cyclopropylmethoxy)-3-pyridyl]oxy]-2-oxo-pyrrolidin-1-yl]imidazo[1,2-a]pyridin-2-yl]acetate,
(3R)-3-[[6-(cyclopropylmethoxy)-3-pyridyl]oxy]-1-(2-methylbenzotriazol-5-yl)pyrrolidin-2-one,
2-[6-[(3R)-3-[[6-(cyclopropylmethoxy)-3-pyridyl]oxy]-2-oxo-pyrrolidin-1-yl]-4-fluorobenzotriazol-2-yl]-N,N-dimethyl-acetamide,
6-[(3R)-3-[[6-(cyclopropylmethoxy)-3-pyridyl]oxy]-2-oxo-pyrrolidin-1-yl]-2-methyl-[1,2,4]triazolo[4,3-a]pyridin-3-one,
2-[6-[(3R)-3-[[6-(cyclopropylmethoxy)-3-pyridyl]oxy]-2-oxo-pyrrolidin-1-yl]-3-oxo-[1,2,4]triazolo[4,3-a]pyridin-2-yl]acetic acid,
6-[(3R)-3-[[6-(cyclopropylmethoxy)-3-pyridyl]oxy]-2-oxo-pyrrolidin-1-yl]-8-fluoro-2H-[1,2,4]triazolo[4,3-a]pyridin-3-one,
methyl 2-[6-[(3R)-3-[[6-(cyclopropylmethoxy)-3-pyridyl]oxy]-2-oxo-pyrrolidin-1-yl]-3-oxo-[1,2,4]triazolo[4,3-a]pyridin-2-yl]acetate,
6-[(3R)-3-[[6-(cyclopropylmethoxy)-3-pyridyl]oxy]-2-oxo-pyrrolidin-1-yl]-8-fluoro-2-methyl-[1,2,4]triazolo[4,3-a]pyridin-3-one,
methyl 2-[6-[(3R)-3-[[6-(cyclopropylmethoxy)-3-pyridyl]oxy]-2-oxo-pyrrolidin-1-yl]-8-fluoro-3-oxo-[1,2,4]triazolo[4,3-a]pyridin-2-yl]acetate,
(R)-2-(6-(3-((6-(cyclopropylmethoxy)pyridin-3-yl)oxy)-2-oxopyrrolidin-1-yl)-8-fluoro-3-oxo-[1,2,4]triazolo[4,3-a]pyridin-2(3H)-yl)acetic acid,
2-[6-[(3R)-3-[[6-(cyclopropylmethoxy)-3-pyridyl]oxy]-2-oxo-pyrrolidin-1-yl]-8-fluoro-3-oxo-[1,2,4]triazolo[4,3-a]pyridin-2-yl]-N,N-dimethyl-acetamide,
N-cyclopropyl-2-[6-[(3R)-3-[[6-(cyclopropylmethoxy)-3-pyridyl]oxy]-2-oxo-pyrrolidin-1-yl]-8-fluoro-3-oxo-[1,2,4]triazolo[4,3-a]pyridin-2-yl]acetamide,
2-[5-[(3R)-3-[[6-(cyclopropylmethoxy)-3-pyridyl]oxy]-2-oxo-pyrrolidin-1-yl]benzotriazol-2-yl]-N,N-dimethyl-acetamide,
2-[5-[(3R)-3-[[6-(cyclopropylmethoxy)-3-pyridyl]oxy]-2-oxo-pyrrolidin-1-yl]benzotriazol-2-yl]-N-(2-hydroxyethyl)acetamide,
2-[5-[(3R)-3-[[6-(cyclopropylmethoxy)-3-pyridyl]oxy]-2-oxo-pyrrolidin-1-yl]benzotriazol-2-yl]acetamide,
6-[(3R)-3-[[6-(4-fluorophenoxy)-3-pyridyl]oxy]-2-oxo-pyrrolidin-1-yl]-2-(methylsulfonylmethyl)-[1,2,4]triazolo[4,3-a]pyridin-3-one,
6-[(3R)-3-[4-(cyclopropanecarbonyl)phenoxy]-2-oxo-pyrrolidin-1-yl]-2-(methylsulfonylmethyl)-[1,2,4]triazolo[4,3-a]pyridin-3-one,
2-(methylsulfonylmethyl)-6-[(3R)-2-oxo-3-[[6-(2,2,2-trifluoroethoxy)-3-pyridyl]oxy]pyrrolidin-1-yl]-[1,2,4]triazolo[4,3-a]pyridin-3-one, and
N,N-dimethyl-2-[5-[(3R)-2-oxo-3-[[6-(2,2,2-trifluoroethoxy)-3-pyridyl]oxy]pyrrolidin-1-yl]indazol-2-yl]acetamide.

In another embodiment compounds of the formula I are encompassed selected from the following list:
2-[6-[(3R)-3-[[6-(Cyclopropylmethoxy)-3-pyridyl]oxy]-2-oxo-pyrrolidin-1-yl]-3-oxo-[1,2,4]triazolo[4,3-a]pyridin-2-yl]-N,N-dimethyl-acetamide,
2-[6-[(3R)-3-[[6-(4-fluorophenoxy)-3-pyridyl]oxy]-2-oxo-pyrrolidin-1-yl]-3-oxo-[1,2,4]triazolo[4,3-a]pyridin-2-yl]-N,N-dimethyl-acetamide,
2-[6-[(3R)-3-[4-(2-cyclopropylacetyl)phenoxy]-2-oxo-pyrrolidin-1-yl]-3-oxo-[1,2,4]triazolo[4,3-a]pyridin-2-yl]-N,N-dimethyl-acetamide,
2-[6-[(3R)-3-[4-(2-cyclopropylacetyl)phenoxy]-2-oxo-pyrrolidin-1-yl]-8-fluoro-3-oxo-[1,2,4]triazolo[4,3-a]pyridin-2-yl]-N,N-dimethyl-acetamide,
2-[6-[(3R)-3-[[6-(cyclopropylmethoxy)-3-pyridyl]oxy]-2-oxo-pyrrolidin-1-yl]-8-fluoro-3-oxo-[1,2,4]triazolo[4,3-a]pyridin-2-yl]-N,N-dimethyl-acetamide and
N-cyclopropyl-2-[6-[(3R)-3-[[6-(cyclopropylmethoxy)-3-pyridyl]oxy]-2-oxo-pyrrolidin-1-yl]-8-fluoro-3-oxo-[1,2,4]triazolo[4,3-a]pyridin-2-yl]acetamide.

In another embodiment the compound of the formula I is 2-[6-[(3R)-3-[[6-(4-fluorophenoxy)-3-pyridyl]oxy]-2-oxo-pyrrolidin-1-yl]-3-oxo-[1,2,4]triazolo[4,3-a]pyridin-2-yl]-N,N-dimethyl-acetamide.

In another embodiment the compound of the formula I is N,N-dimethyl-2-[3-oxo-6-[(3R)-2-oxo-3-[[6-(2,2,2-trifluoroethoxy)-3-pyridyl]oxy]pyrrolidin-1-yl]-[1,2,4]triazolo[4,3-a]pyridin-2-yl]acetamide.

In another embodiment the compound of the formula I is 2-[6-[(3R)-3-[[6-(cyclopropylmethoxy)-3-pyridyl]oxy]-2-oxo-pyrrolidin-1-yl]-8-fluoro-3-oxo-[1,2,4]triazolo[4,3-a]pyridin-2-yl]-N,N-dimethyl-acetamide.

In another embodiment the compound of the formula I is N-cyclopropyl-2-[6-[(3R)-3-[[6-(cyclopropylmethoxy)-3-pyridyl]oxy]-2-oxo-pyrrolidin-1-yl]-8-fluoro-3-oxo-[1,2,4]triazolo[4,3-a]pyridin-2-yl]acetamide.

In another embodiment compounds of the formula I are encompassed selected from the following list:
6-[(3R)-3-[[6-(4-fluorophenoxy)-3-pyridyl]oxy]-2-oxo-pyrrolidin-1-yl]-2-(methylsulfonylmethyl)-[1,2,4]triazolo[4,3-a]pyridin-3-one,
6-[(3R)-3-[4-(cyclopropanecarbonyl)phenoxy]-2-oxo-pyrrolidin-1-yl]-2-(methylsulfonylmethyl)-[1,2,4]triazolo[4,3-a]pyridin-3-one,
2-(methylsulfonylmethyl)-6-[(3R)-2-oxo-3-[[6-(2,2,2-trifluoroethoxy)-3-pyridyl]oxy]pyrrolidin-1-yl]-[1,2,4]triazolo[4,3-a]pyridin-3-one, and
N,N-dimethyl-2-[5-[(3R)-2-oxo-3-[[6-(2,2,2-trifluoroethoxy)-3-pyridyl]oxy]pyrrolidin-1-yl]indazol-2-yl]acetamide.

Structural elements such as groups, substituents, hetero ring members, numbers or other features, for example alkyl groups, groups like $R_5$, $R_5'$, $R_7$, $R_7'$ etc., which can occur several times in the compounds of the formula I, can all independently of one another have at each occurrence any of the indicated meanings and can in each case be identical to or different from one another. For example, the alkyl groups in a dialkylamino group can be identical or different.

Herein, the terms "including" and "comprising" are used in their open, non-limiting sense. As used herein, the terms "$C_1$-$C_6$" and so forth refer to moieties having 1 to 6 carbon atoms and so forth, respectively. Within composed terms like "hydroxy-($C_0$-$C_4$)-alkyl" the option "($C_0$)-alkyl refers to a bond (i.e. in this case a directly bound hydroxy group), or in case of an unsubstituted "($C_0$)-alkyl" it refers to a hydrogen.

The term "alkyl", as used herein, refers to saturated, monovalent hydrocarbon radicals. The term "alkenyl", as used herein, refers to monovalent hydrocarbon radicals, which contain at least one carbon-carbon double bond, wherein each double bond can have E- or Z-configuration. The term "alkynyl", as used herein, refers to monovalent hydrocarbon radicals, which contain at least one carbon-carbon triple bond. The alkyl, alkenyl and alkynyl groups can be linear, i.e. straight-chain, or branched. This also applies when they are part of other groups, for example alkyloxy groups (=alkoxy groups, O-alkyl groups), alkyloxycarbonyl groups or alkyl-substituted amino groups, or when they are substituted. Depending on the respective definition, the number of carbon atoms in an alkyl group can be 1, 2, 3, 4, 5 or 6, or 1, 2, 3, or 4. Examples of alkyl are methyl, ethyl, propyl including n-propyl and isopropyl, butyl including n-butyl, sec-butyl, isobutyl and tert-butyl, pentyl including n-pentyl, 1-methylbutyl, isopentyl, neopentyl and tert-pentyl, hexyl including n-hexyl, 3,3-dimethylbutyl and isohexyl. Double bonds and triple bonds in alkenyl groups and alkynyl groups respectively can be present in any positions. Examples of alkenyl and alkynyl are ethenyl, prop-1-enyl, prop-2-enyl (=allyl), but-2-enyl, 2-methylprop-2-enyl, 3-methylbut-2-enyl, hex-3-enyl, hex-4-enyl, prop-2-ynyl (=propargyl), but-2-ynyl, but-3-ynyl, hex-4-ynyl or hex-5-ynyl. Substituted alkyl groups, alkenyl groups and alkynyl groups can be substituted in any positions, provided that the respective compound is sufficiently stable and is suitable for the desired purpose such as use as a drug substance. The prerequisite that a specific group and a compound of the formula I are sufficiently stable and suitable for the desired purpose such as use as a drug substance, applies in general with respect to the definitions of all groups in the compounds of the formula I.

Independently of one another and independently of any other substituents, alkyl groups, divalent alkyl groups, alkenyl groups, alkynyl groups, cycloalkyl groups and heterocycloalkyl groups are optionally substituted by one or more fluorine substituents which can be located in any positions, i.e., the said groups can be unsubstituted by fluorine substituents or substituted by fluorine substituents, for example by 1, 2 or 3, by 1 or 2, or by 1 fluorine substituents. Examples of fluorine-substituted said groups are trifluoromethyl, difluoromethyl and fluoromethyl.

The term "alkanediyl" or "alkylene", as used herein, refers to saturated, divalent hydrocarbon radicals. The term "alkenediyl", as used herein, refers to divalent hydrocarbon radicals, which contain at least one carbon-carbon double bond, wherein each double bond can have E- or Z-configuration. The term "alkynediyl", as used herein, refers to divalent hydrocarbon radicals, which contain at least one carbon-carbon triple bond. As far as applicable, the preceding explanations regarding alkyl, alkenyl and alkynyl groups apply correspondingly to alkanediyl, alkenediyl and alkynediyl groups, which thus can likewise be linear and branched. Examples of divalent alkyl groups are —CH$_2$— (=methylene), —CH$_2$—CH$_2$—, —CH$_2$—CH$_2$—CH$_2$—, —CH$_2$—CH$_2$—CH$_2$—CH$_2$—, —CH(CH$_3$)—, —C(CH$_3$)$_2$—, —CH(CH$_3$)—CH$_2$—, —CH$_2$—CH(CH$_3$)—, —C(CH$_3$)$_2$—CH$_2$— and —CH$_2$—C(CH$_3$)$_2$—.

The term "cycloalkyl", as used herein, unless otherwise indicated, refers to a monovalent radical of a saturated hydrocarbon ring system, which is monocyclic. In a monocyclic cycloalkyl group the number of ring carbon atoms can be for example 3, 4, 5, 6, 7 or 8. In one embodiment of the invention, the number of ring carbon atoms in a cycloalkyl group, independently of the number of ring carbon atoms in any other cycloalkyl group is 3, 4, 5 or 6, in another embodiment 3 or 4, in another embodiment 3, in another embodiment 5 or 6, in another embodiment 5, in another embodiment 6. Examples of cycloalkyl groups are cyclopropyl, cyclobutyl, cyclopentyl and cyclohexyl. The term "heterocycle", as used herein, unless otherwise indicated, refers to a cycloalkyl as defined above, in which 1, 2, 3 or 4 carbon atoms are replaced by nitrogen or oxygen atoms, provided that the heterocycloalkyl system is stable and suitable as a subgroup for the desired purpose of the compound of the formula I such as use as a drug substance. Depending on the definition of the respective heterocyclic group, in one embodiment of the invention the number of ring heteroatoms which can be present in a heterocyclic group, independently of the number of ring heteroatoms in any other heterocyclic group, is 1 or 2, in another embodiment 2, in another embodiment 1, wherein the ring heteroatoms can be identical or different. The heterocycloalkyl group can be attached by any ring carbon atom or saturated ring nitrogen atom, with the exception of spiro- or bridgehead atoms.

Exemplary monocyclic heterocycloalkyl groups are derived from, but not limited to, the ring systems azetidine, oxetane, pyrrolidine, tetrahydrofuran, 1,3-dioxolane, piperidine, piperazine, morpholine, tetrahydropyran or 1,4-dioxane:

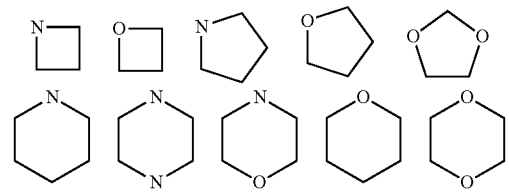

In one embodiment monocyclic heterocycloalkyl groups are derived from azetidine, pyrrolidine, piperidine, piperazine or morpholine:

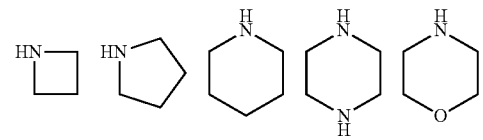

The term "aryl", as used herein, refers to a radical derived from an aromatic hydrocarbon by removal of one hydrogen, such as phenyl.

The term "heteroaryl" as used herein, refers to a radical derived from a fully unsaturated monocyclic ring system, in which 1, 2 or 3 carbon atoms are replaced by heteroatoms. The ring heteroatoms are generally chosen from N, O and S, wherein N includes ring nitrogen atoms which carry a hydrogen atom or a substituent as well as ring nitrogen atoms which do not carry a hydrogen atom or a substituent. Ring heteroatoms can be located in any position, provided that the heterocyclic system is stable and suitable as a subgroup for the desired purpose of the compound of the formula I such as use as a drug substance. Heteroaryl radicals are derived from 5-membered or 6-membered monocyclic rings.

Exemplary heteroaryl systems are derived from, but not limited to, the following ring systems: pyrrole, furan, thiophene, imidazole, pyrazole, oxazole (=[1,3]oxazole), isoxazole (=[1,2]oxazole), thiazole (=[1,3]thiazole), isothiazole (=[1,2]thiazole), [1,2,3]triazole, [1,2,4]triazole, [1,2,4]oxadiazole, [1,3,4]oxadiazole, [1,2,4]thiadiazole, [1,3,4]thiadiazole, pyridine, pyridazine, pyrimidine, pyrazine, [1,2,3]triazine, [1,2,4]triazine or [1,3,5]triazine:

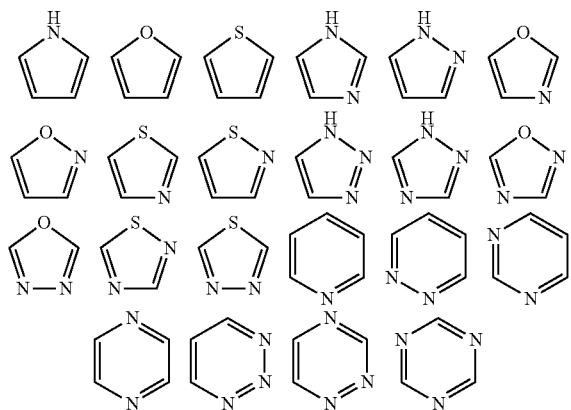

Groups like phenyl and residues of aromatic heterocycles which are optionally substituted by one or more substituents, can be unsubstituted or substituted, for example by 1, 2 or 3, or by 1 or 2, or by 1, identical or different substituents which can be located in any positions. Aromatic nitrogen heterocycles which in the parent ring system carry a hydrogen atom on a ring nitrogen atom in a 5-membered ring, such as a pyrrole or imidazole ring, for example, can be substituted on ring carbon atoms and/or on such ring nitrogen atoms. In one embodiment of the invention, substituents on such ring nitrogen atoms are chosen from $(C_1$-$C_4)$-alkyl groups, i.e. such ring nitrogen atoms in aromatic heterocycles carry a hydrogen atom or a $(C_1$-$C_4)$-alkyl substituent. When it is stated with respect to ring nitrogen atoms in aromatic heterocycles and any other heterocycles that they can carry a hydrogen atom or a substituent, such ring nitrogen atoms either carry a hydrogen atom or a substituent or they do not carry a hydrogen atom or substituent. Ring nitrogen atoms which carry a hydrogen atom or a substituent, occur in a nitrogen-containing aromatic 5-membered ring as is present in pyrrole or imidazole for example, and in a non-aromatic ring including a saturated ring. Ring nitrogen atoms which do not carry a hydrogen atom or a substituent unless they are present in positively charged form, including any further ring nitrogen atoms in addition to ring nitrogen atoms which carry a hydrogen atom or a substituent, occur in an aromatic ring as is present in thiazole, imidazole or pyridine, for example, and in a non-aromatic ring in which they are part of a double bond, and they occur as ring nitrogen atoms via which a ring is bonded. Suitable ring nitrogen atoms in aromatic heterocycles in the compounds of the formula I, such as the ring nitrogen atom in a pyridine ring, can in general also be present as N-oxide or as quaternary salt, for example as N—$(C_1$-$C_4)$-alkyl salt such as N-methyl salt, wherein in one embodiment of the invention the counter anion in such quaternary salt is a physiologically acceptable anion which is derived from an acid that forms a physiologically acceptable salt.

In monosubstituted phenyl groups, the substituent can be located in the 2-position, the 3-position or the 4-position. In disubstituted phenyl groups, the substituents can be located in 2,3-position, 2,4-position, 2,5-position, 2,6-position, 3,4-position or 3,5-position. In trisubstituted phenyl groups, the substituents can be located in 2,3,4-position, 2,3,5-position, 2,3,6-position, 2,4,5-position, 2,4,6-position or 3,4,5-position.

Ring heteroatoms can be located in any positions, provided that the heterocyclic system is known in the art and is stable and suitable as a subgroup for the desired purpose of the compound of the formula I such as use as a drug substance. In one embodiment of the invention, two ring oxygen atoms cannot be present in adjacent ring positions of any heterocycle, in another embodiment two ring heteroatoms chosen from oxygen and sulfur cannot be present in adjacent ring positions of any heterocycle. Substituents on heterocyclic groups can be located in any positions. For example, in a pyridin-2-yl group substituents can be located in the 3-position and/or 4-position and/or 5-position and/or 6-position, in a pyridin-3-yl group substituent can be located in the 2-position and/or 4-position and/or 5-position and/or 6-position, in a pyridin-4-yl group substituents can be located in the 2-position and/or 3-position and/or 5-position and/or 6-position.

When an oxo group is bonded to a carbon atom, it replaces two hydrogen atoms on a carbon atom of the parent system. Thus, if a $CH_2$ group in a chain or a ring is substituted by oxo, i.e. by a doubly bonded oxygen atom, it becomes a CO group. Evidently, an oxo group cannot occur as a substituent on a carbon atom in an aromatic ring such as in a phenyl group, for example.

The present invention includes all stereoisomeric forms of the compounds of the formula I and their salts and solvates. With respect to each chiral center, independently of any other chiral center, the compounds of the formula I can be present in S configuration or substantially S configuration, or in R configuration or substantially R configuration, or as a mixture of the S isomer and the R isomer in any ratio. The invention includes all possible enantiomers and diastereomers and mixtures of two or more stereoisomers, for example mixtures of enantiomers and/or diastereomers, in all ratios. Thus, compounds according to the invention which can exist as enantiomers can be present in enantiomerically pure form, both as levorotatory and as dextrorotatory antipodes, and in the form of mixtures of the two enantiomers in all ratios including racemates. In the case of a E/Z isomerism, or cis/trans isomerism, for example on double bonds or rings such as cycloalkyl rings, the invention includes both the E form and Z form, or the cis form and the trans form, as well as mixtures of these forms in all ratios. In one embodiment of the invention, a compound which can occur in two or more stereoisomeric forms is a pure, or substantially pure, individual stereoisomer. The preparation of individual stereoisomers can be carried out, for example, by separation of a mixture of isomers by customary methods, for example by chromatography or crystallization, by the use of stereochemically uniform starting materials in the synthesis, or by stereoselective synthesis. Optionally, a derivatization can be carried out before a separation of stereoisomers. The separation of a mixture of stereoisomers can be carried out at the stage of the compound of the formula I or at the stage of a starting material or an intermediate during the synthesis. The present invention also includes all tautomeric forms of the compounds of the formula I and their salts and solvates.

In case the compounds of the formula I contain one or more acidic and/or basic groups, i.e. salt-forming groups, the invention also includes their corresponding physiologically or toxicologically acceptable salts, i.e. non-toxic salts, in particular their pharmaceutically acceptable salts.

The present invention furthermore includes all solvates of compounds of the formula I, for example hydrates or adducts with alcohols such as $(C_1-C_4)$-alkanols, active metabolites of the compounds of the formula I, and also prodrugs and derivatives of the compounds of the formula I which in vitro may not necessarily exhibit pharmacological activity but which in vivo are converted into pharmacologically active compounds, for example esters or amides of carboxylic acid groups.

The compounds of the present invention can be widely combined with other pharmacologically active compounds, such as all drugs mentioned in the Rote Liste 2014, e.g. all antidiabetics mentioned in the Rote Liste 2014, chapter 12, all weight-reducing agents or appetite suppressants mentioned in the Rote Liste 2014, chapter 06, all lipid-lowering agents mentioned in the Rote Liste 2014, chapter 58, all antihypertensives mentioned in the Rote Liste 2014 chapter 17, all nephroprotectives mentioned in the Rote Liste, or all diuretics mentioned in the Rote Liste 2014, chapter 36.

The active ingredient combinations can be applied either by separate administration of the active ingredients to the patient or in the form of combination products in which a plurality of active ingredients are present in one pharmaceutical preparation. When administered separately, administration may occur simultaneously or sequentially, in any order. The amount of the compound of the invention and the other pharmaceutically active ingredient(s) and the relative timings of administration will be selected in order to achieve the desired combined therapeutic effect. The administration of the combination may be concomitantly in: (1) a unitary pharmaceutical composition including all pharmaceutically active ingredients; or (2) separate pharmaceutical compositions each including at least one of the pharmaceutically active ingredients. Alternatively, the combination may be administered separately in a sequential manner wherein one treatment agent is administered first and the other second or vice versa. Such sequential administration may be close in time or remote in time.

Most of the active ingredients mentioned hereinafter are disclosed in the USP Dictionary of USAN and International Drug Names, US Pharmacopeia, Rockville 2014.

Therapeutic agents which are suitable for combinations include, for example, antidiabetic agents such as:

Insulin and insulin derivatives, for example: insulin glargine (e.g. Lantus®), higher than 100 U/mL concentrated insulin glargine, e.g. 270-330 U/mL of insulin glargine or 300 U/mL of insulin glargine (as disclosed in EP 2387989), insulin glulisine (e.g. Apidra®), insulin detemir (e.g. Levemir®), insulin lispro (e.g. Humalog®, Liprolog®), insulin degludec (e.g. DegludecPlus®, IdegLira (NN9068)), insulin aspart and aspart formulations (e.g. NovoLog®), basal insulin and analogues (e.g. LY2605541, LY2963016, NN1436), PEGylated insulin lispro (e.g. LY-275585), long-acting insulins (e.g. NN1436, Insumera (PE0139), AB-101, AB-102, Sensulin LLC), intermediate-acting insulins (e.g. Humulin®N, Novolin®N), fast-acting and short-acting insulins (e.g. Humulin®R, Novolin®R, Linjeta®(VIAject®), PH20 insulin, NN1218, HinsBet®), premixed insulins, SuliXen®, NN1045, insulin plus Symlin®, PE-0139, ACP-002 hydrogel insulin, and oral, inhalable, transdermal and buccal or sublingual insulins (e.g. Exubera®, Nasulin®, Afrezza®, insulin tregopil, TPM-02 insulin, Capsulin®, Oral-Lyn®, Cobalamin® oral insulin, ORMD-0801, Oshadi oral insulin, NN1953, NN1954, NN1956, VIAtab®). Also suitable are those insulin derivatives which are bonded to albumin or another protein by a bifunctional linker.

Glucagon-like-peptide 1 (GLP-1), GLP-1 analogues, and GLP-1 receptor agonists, for example: lixisenatide (e.g. Lyxumia®), exenatide (e.g. exendin-4, rExendin-4, Byetta®, Bydureon®, exenatide NexP), liraglutide (e.g. Victoza®), semaglutide, taspoglutide, albiglutide, dulaglutide, ACP-003, CJC-1134-PC, GSK-2374697, PB-1023, TTP-054, langlenatide (HM-11260C), CM-3, GLP-1 Eligen, AB-201, ORMD-0901, NN9924, NN9926, NN9927, Nodexen, Viador-GLP-1, CVX-096, ZYOG-1, ZYD-1, ZP-3022, CAM-2036, DA-3091, DA-15864, ARI-2651, ARI-2255, exenatide-XTEN (VRS-859), exenatide-XTEN+ Glucagon-XTEN (VRS-859+AMX-808) and polymer-bound GLP-1 and GLP-1 analogues.

Dual GLP-1/GIP agonists (e.g. RG-7697 (MAR-701), MAR-709, BHM081, BHM089, BHM098).

Dual GLP-1/glucagon receptor agonists (e.g. BHM-034, OAP-189 (PF-05212389, TKS-1225), TT-401/402, ZP2929, LAPS-HMOXM25, MOD-6030).

Dual GLP-1/gastrin agonists (e.g. ZP-3022).

Other suitable combination partners are:

Further gastrointestinal peptides such as peptide YY 3-36 (PYY3-36) or analogues thereof and pancreatic polypeptide (PP) or analogues thereof.

Glucagon receptor agonists or antagonists, glucose-dependent insulinotropic polypeptide (GIP) receptor agonists or antagonists, ghrelin antagonists or inverse agonists, xenin and analogues thereof.

Dipeptidyl peptidase-IV (DPP-4) inhibitors, for example: alogliptin (e.g. Nesina®, Kazano®), linagliptin (e.g. Ondero®, Trajenta®, Tradjenta®, Trayenta®), saxagliptin (e.g. Onglyza®, Komboglyze XR®), sitagliptin (e.g. Januvia®, Xelevia®, Tesavel®, Janumet®, Velmetia®, Juvisync, Janumet XR®), anagliptin, teneligliptin (e.g. Tenelia®), trelagliptin, vildagliptin (e.g. Galvus®, Galvumet®), gemigliptin, omarigliptin, evogliptin, dutogliptin, DA-1229, MK-3102, KM-223, KRP-104, PBL-1427, Pinoxacin hydrochloride, and Ari-2243.

Sodium-dependent glucose transporter 2 (SGLT-2) inhibitors, for example: canagliflozin, dapagliflozin, remogliflozin, remogliflozin etabonate, sergliflozin, empagliflozin, ipragliflozin, tofogliflozin, luseogliflozin, ertugliflozin, EGT-0001442, LIK-066, SBM-TFC-039, and KGA-3235 (DSP-3235).

Dual inhibitors of SGLT-2 and SGLT-1 (e.g. LX-4211, LIK066).

SGLT-1 inhibitors (e.g. LX-2761, KGA-3235) or SGLT-1 inhibitors in combination with anti-obesity drugs such as ileal bile acid transfer (IBAT) inhibitors (e.g. GSK-1614235+GSK-2330672).

Biguanides (e.g. metformin, buformin, phenformin).

Thiazolidinediones (e.g. pioglitazone, rosiglitazone), glitazone analogues (e.g. lobeglitazone).

Peroxisome proliferator-activated receptors (PPAR-)(alpha, gamma or alpha/gamma) agonists or modulators (e.g. saroglitazar (e.g. Lipaglyn®), GFT-505), or PPAR gamma partial agonists (e.g. Int-131).

Sulfonylureas (e.g. tolbutamide, glibenclamide, glimepiride, Amaryl®, glipizide) and meglitinides (e.g. nateglinide, repaglinide, mitiglinide).

Alpha-glucosidase inhibitors (e.g. acarbose, miglitol, voglibose).

Amylin and amylin analogues (e.g. pramlintide, Symlin®).

G-protein coupled receptor 119 (GPR119) agonists (e.g. GSK-1292263, PSN-821, MBX-2982, APD-597, ARRY-981, ZYG-19, DS-8500, HM-47000, YH-Chem1).

GPR40 agonists (e.g. TUG-424, P-1736, P-11187, JTT-851, GW9508, CNX-011-67, AM-1638, AM-5262).

GPR120 agonists and GPR142 agonists.

Systemic or low-absorbable TGR5 (GPBAR1=G-protein-coupled bile acid receptor 1) agonists (e.g. INT-777, XL-475, SB756050).

Other suitable combination partners are:

Diabetes immunotherapeutics, for example: oral C—C chemokine receptor type 2 (CCR-2) antagonists (e.g. CCX-140, JNJ-41443532), interleukin 1 beta (IL-1β) antagonists (e.g. AC-201), or oral monoclonal antibodies (MoA) (e.g. methalozamide, VVP808, PAZ-320, P-1736, PF-05175157, PF-04937319).

Anti-inflammatory agents for the treatment of the metabolic syndrome and diabetes, for example: nuclear factor kappa B inhibitors (e.g. Triolex®).

Adenosine monophosphate-activated protein kinase (AMPK) stimulants, for example: Imeglimin (PXL-008), Debio-0930 (MT-63-78), R-118.

Inhibitors of 11-beta-hydroxysteroid dehydrogenase 1 (11-beta-HSD-1) (e.g. LY2523199, BMS770767, RG-4929, BMS816336, AZD-8329, HSD-016, BI-135585).

Activators of glucokinase (e.g. PF-04991532, TTP-399 (GK1-399), GKM-001 (ADV-1002401), ARRY-403 (AMG-151), TAK-329, TMG-123, ZYGK1).

Inhibitors of diacylglycerol O-acyltransferase (DGAT) (e.g. pradigastat (LCQ-908)), inhibitors of protein tyrosine phosphatase 1 (e.g. trodusquemine), inhibitors of glucose-6-phosphatase, inhibitors of fructose-1,6-bisphosphatase, inhibitors of glycogen phosphorylase, inhibitors of phosphoenol pyruvate carboxykinase, inhibitors of glycogen synthase kinase, inhibitors of pyruvate dehydrogenase kinase.

Modulators of glucose transporter-4, somatostatin receptor 3 agonists (e.g. MK-4256).

One or more lipid lowering agents are also suitable as combination partners, for example: 3-hydroxy-3-methylglutaryl-coenzym-A-reductase (HMG-CoA-reductase) inhibitors such as simvastatin (e.g. Zocor®, Inegy®, Simcor®), atorvastatin (e.g. Sortis®, Caduet®), rosuvastatin (e.g. Crestor®), pravastatin (e.g. Lipostat®, Selipran®), fluvastatin (e.g. Lescol®), pitavastatin (e.g. Livazo®, Livalo®), lovastatin (e.g. Mevacor®, Advicor®), mevastatin (e.g. Compactin®), rivastatin, cerivastatin (Lipobay®), fibrates such as bezafibrate (e.g. Cedur® retard), ciprofibrate (e.g. Hyperlipen®), fenofibrate (e.g. Antara®, Lipofen®, Lipanthyl®), gemfibrozil (e.g. Lopid®, Gevilon®), etofibrate, simfibrate, ronifibrate, clinofibrate, clofibride, nicotinic acid and derivatives thereof (e.g. niacin, including slow release formulations of niacin), nicotinic acid receptor 1 agonists (e.g. GSK-256073), PPAR-delta agonists, acetyl-CoA-acetyltransferase (ACAT) inhibitors (e.g. avasimibe), cholesterol absorption inhibitors (e.g. ezetimibe, Ezetrol®, Zetia®, Liptruzet®, Vytorin®, S-556971), bile acid-binding substances (e.g. cholestyramine, colesevelam), ileal bile acid transport (IBAT) inhibitors (e.g. GSK-2330672, LUM-002), microsomal triglyceride transfer protein (MTP) inhibitors (e.g. lomitapide (AEGR-733), SLx-4090, granotapide), modulators of proprotein convertase subtilisin/kexin type 9 (PCSK9) (e.g. alirocumab (REGN727/SAR236553), AMG-145, LGT-209, PF-04950615, MPSK3169A, LY3015014, ALD-306, ALN-PCS, BMS-962476, SPC5001, ISIS-394814, 1B20, LGT-210, 1D05, BMS-PCSK9Rx-2, SX-PCK9, RG7652), LDL receptor up-regulators, for example liver selective thyroid hormone receptor beta agonists (e.g. eprotirome (KB-2115), MB07811, sobetirome (QRX-431), VIA-3196, ZYT1), HDL-raising compounds such as: cholesteryl ester transfer protein (CETP) inhibitors (e.g. anacetrapib (MK0859), dalcetrapib, evacetrapib, JTT-302, DRL-17822, TA-8995, R-1658, LY-2484595, DS-1442), or dual CETP/PCSK9 inhibitors (e.g. K-312), ATP-binding cassette (ABC1) regulators, lipid metabolism modulators (e.g. BMS-823778, TAP-301, DRL-21994, DRL-21995), phospholipase A2 (PLA2) inhibitors (e.g. darapladib, Tyrisa®, varespladib, rilapladib), ApoA-I enhancers (e.g. RVX-208, CER-001, MDCO-216, CSL-112), cholesterol synthesis inhibitors (e.g. ETC-1002), lipid metabolism modulators (e.g. BMS-823778, TAP-301, DRL-21994, DRL-21995) and omega-3 fatty acids and derivatives thereof (e.g. icosapent ethyl (AMR101), Epanova®, AKR-063, NKPL-66, PRC-4016, CAT-2003).

Other suitable combination partners are one or more active substances for the treatment of obesity, such as for example:

Bromocriptine (e.g. Cycloset®, Parlodel®), phentermine and phentermine formulations or combinations (e.g. Adipex-P, Ionamin, Qsymia®), benzphetamine (e.g. Didrex®), diethylpropion (e.g. Tenuate®), phendimetrazin (e.g. Adipost®, Bontril®), bupropion and combinations (e.g. Zyban®, Wellbutrin XL®, Contrave®, Empatic®), sibutramine (e.g. Reductil®, Meridia®), topiramat (e.g. Topamax®), zonisamid (e.g. Zonegran), tesofensine, opioid antagonists such as naltrexone (e.g. Naltrexin®, naltrexone+bupropion), cannabinoid receptor 1 (CB1) antagonists (e.g. TM-38837), melanin-concentrating hormone (MCH-1) antagonists (e.g. BMS-830216, ALB-127158(a)), MC4 receptor agonists and partial agonists (e.g. AZD-2820, RM-493), neuropeptide Y5 (NPY5) or NPY2 antagonists (e.g. velneperit, S-234462), NPY4 agonists (e.g. PP-1420), beta-3-adrenergic receptor agonists, leptin or leptin mimetics, agonists of the 5-hydroxytryptamine 2c (5HT2c) receptor (e.g. lorcaserin, Belviq®), pramlintide/metreleptin, lipase inhibitors such as cetilistat (e.g. Cametor®), orlistat (e.g. Xenical®, Calobalin®), angiogenesis inhibitors (e.g. ALS-L1023), betahistidin and histamine H3 antagonists (e.g. HPP-404), AgRP (agouti related protein) inhibitors (e.g. TTP-435), serotonin re-uptake inhibitors such as fluoxetine (e.g. Fluctine®), duloxetine (e.g. Cymbalta®), dual or triple monoamine uptake inhibitors (dopamine, norepinephrine and serotonin re-uptake) such as sertraline (e.g. Zoloft®), tesofensine, methionine aminopeptidase 2 (MetAP2) inhibitors (e.g. beloranib), and antisense oligonucleotides against production of fibroblast growth factor receptor 4 (FGFR4) (e.g. ISIS-FGFR4Rx) or prohibitin targeting peptide-1 (e.g. Adipotide®).

Moreover, combinations with drugs for influencing high blood pressure, chronic heart failure or atherosclerosis, for example: nitric oxide donors, AT1 antagonists or angiotensin II (AT2) receptor antagonists such as telmisartan (e.g. Kinzal®, Micardis®), candesartan (e.g. Atacand®, Blopress®), valsartan (e.g. Diovan®, Co-Diovan®), losartan (e.g. Cosaar®), eprosartan (e.g. Teveten®), irbesartan (e.g. Aprovel®, CoAprovel®), olmesartan (e.g. Votum®, Olmetec®), tasosartan, azilsartan (e.g. Edarbi®), dual angiotensin receptor blockers (dual ARBs), angiotensin converting enzyme (ACE) inhibitors, ACE-2 activators, renin inhibitors, prorenin inhibitors, endothelin converting enzyme (ECE) inhibitors, endothelin receptor (ET1/ETA) blockers, endothelin antagonists, diuretics, aldosterone antagonists, aldosterone synthase inhibitors, alpha-blockers, antagonists of the alpha-2 adrenergic receptor, beta-blockers, mixed alpha/beta-blockers, calcium antagonists, calcium channel blockers (CCBs), nasal formulations of the calcium channel blocker diltiazem (e.g. CP-404), dual mineralocorticoid/

CCBs, centrally acting antihypertensives, inhibitors of neutral endopeptidase, aminopeptidase-A inhibitors, vasopeptide inhibitors, dual vasopeptide inhibitors such as neprilysin-ACE inhibitors or neprilysin-ECE inhibitors, dual-acting AT receptor-neprilysin inhibitors, dual AT1/ETA antagonists, advanced glycation end-product (AGE) breakers, recombinant renalase, blood pressure vaccines such as anti-RAAS (renin-angiotensin-aldosteron-system) vaccines, AT1- or AT2-vaccines, drugs based on hypertension pharmacogenomics such as modulators of genetic polymorphisms with antihypertensive response, thrombocyte aggregation inhibitors, and others or combinations thereof are suitable.

In another aspect, this invention relates to the use of a compound according to the invention or a physiologically acceptable salt thereof combined with at least one of the active substances described above as a combination partner, for preparing a medicament which is suitable for the treatment or prevention of diseases or conditions which can be affected by binding to the GPR119 and modulating its activity. This is preferably a disease in the context of the metabolic syndrome, particularly one of the diseases or conditions listed above, most particularly diabetes or obesity or complications thereof.

The use of the compounds according to the invention, or a physiologically acceptable salt thereof, in combination with one or more active substances may take place simultaneously, separately or sequentially.

The use of the compound according to the invention, or a physiologically acceptable salt thereof, in combination with another active substance may take place simultaneously or at staggered times, but particularly within a short space of time. If they are administered simultaneously, the two active substances are given to the patient together; if they are used at staggered times, the two active substances are given to the patient within a period of less than or equal to 12 hours, but particularly less than or equal to 6 hours.

Consequently, in another aspect, this invention relates to a medicament which comprises compounds according to the invention or a physiologically acceptable salt of such a compound and at least one of the active substances described above as combination partners, optionally together with one or more inert carriers and/or diluents.

The compounds according to the invention, or physiologically acceptable salt or solvate thereof, and the additional active substance to be combined therewith may both be present together in one formulation, for example a tablet or capsule, or separately in two identical or different formulations, for example as so-called kit-of-parts.

Compounds according to the invention can be administered to animals, in particular to mammals including humans, as pharmaceuticals by themselves, in mixtures with one another, or in the form of pharmaceutical compositions. The administration can be carried out orally, for example in the form of tablets, film-coated tablets, sugar-coated tablets, granules, hard and soft gelatin capsules, solutions including aqueous, alcoholic and oily solutions, juices, drops, syrups, emulsions or suspensions, rectally, for example in the form of suppositories, or parenterally, for example in the form of solutions for subcutaneous, intramuscular or intravenous injection or infusion, in particular aqueous solutions.

Suitable pharmaceutical compositions for oral administration may be in the form of separate units, for example capsules, cachets, lozenges or tablets, each of which contains a defined amount of the compound of formula I; as powders or granules; as solution or suspension in an aqueous or nonaqueous liquid; or as an oil-in-water or water-in-oil emulsion. These compositions may, as already mentioned, be prepared by any suitable pharmaceutical method which includes a step in which the active ingredient and the carrier (which may consist of one or more additional ingredients) are brought into contact. The compositions are generally produced by uniform and homogeneous mixing of the active ingredient with a liquid and/or finely divided solid carrier, after which the product is shaped if necessary. Thus, for example, a tablet can be produced by compressing or molding a powder or granules of the compound, where appropriate with one or more additional ingredients. Compressed tablets can be produced by tableting the compound in free-flowing form such as, for example, a powder or granules, where appropriate mixed with a binder, glidant, inert diluent and/or one (or more) surfactant(s)/dispersant(s) in a suitable machine. Molded tablets can be produced by molding the compound, which is in powder form and has been moistened with an inert liquid diluent, in a suitable machine.

Pharmaceutical compositions which are suitable for peroral (sublingual) administration comprise lozenges which contain a compound of formula I with a flavoring, typically sucrose, and gum arabic or tragacanth, and pastilles which comprise the compound in an inert base such as gelatin and glycerol or sucrose and gum arabic.

Coated formulations and coated slow-release formulations, especially acid- and gastric juice-resistant formulations, also belong within the framework of the invention. Suitable coatings resistant to gastric juice comprise cellulose acetate phthalate, polyvinyl acetate phthalate, hydroxypropylmethylcellulose phthalate and anionic polymers of methacrylic acid and methyl methacrylate.

Pharmaceutical compositions suitable for rectal administration are preferably in the form of single-dose suppositories. These can be produced by mixing a compound of formula I with one or more conventional solid carriers, for example cocoa butter, and shaping the resulting mixture.

Pharmaceutical compositions suitable for parenteral administration comprise preferably sterile aqueous preparations of a compound of formula I, which are preferably isotonic with the blood of the intended recipient. These preparations are preferably administered intravenously, although administration may also take place by subcutaneous, intramuscular or intradermal injection. These preparations can preferably be produced by mixing the compound with water and making the resulting solution sterile and isotonic with blood. Injectable compositions of the invention generally contain 0.1 to 5% by weight of the active compound.

Other suitable administration forms are, for example, percutaneous or topical administration, for example in the form of ointments, creams, tinctures, sprays, powders or transdermal therapeutic systems, or inhalative administration, for example in the form of nasal sprays or aerosol mixtures, or forms such as microcapsules, implants or rods.

Pharmaceutical compositions suitable for topical use on the skin are preferably in the form of ointment, cream, lotion, paste, spray, aerosol or oil. The carriers used may be petrolatum, lanolin, polyethylene glycols, alcohols and combinations of two or more of these substances. The active ingredient is generally present in a concentration of 0.1 to 15% by weight of the composition, for example 0.5 to 2%.

Transdermal administration is also possible. Pharmaceutical compositions suitable for transdermal uses may be in the form of single patches which are suitable for long-term close contact with the patient's epidermis. Such patches suitably contain the active ingredient in an aqueous solution which is buffered where appropriate, dissolved and/or dispersed in an adhesive or dispersed in a polymer. A suitable active ingredient concentration is about 1% to 35%, preferably about 3% to 15%. A particular option is for the active ingredient to be released by electrotransport or iontophoresis as described, for example, in Pharmaceutical Research, 2(6): 318 (1986).

Compounds according to the invention can additionally be used in systems for local drug delivery, for example in coated stents for preventing or reducing in-stent restenosis or by applying them locally by means of a catheter. The appropriate administration form depends, among others, on the disease to be treated and on its severity.

The dosing of compounds according to the invention to achieve the desirable therapeutic effect depends on a number of factors, for example the specific compound chosen, the intended use, the mode of administration and the clinical condition of the patient. The daily dose is generally in the range from 0.3 mg to 100 mg (typically from 3 mg to 50 mg) per day and per kilogram of body weight, for example 3-10 mg/kg/day. An intravenous dose may be, for example, in the range from 0.3 mg to 1.0 mg/kg, which can suitably be administered as infusion of 10 ng to 100 ng per kilogram and per minute. Suitable infusion solutions for these purposes may contain, for example, 0.1 ng to 100 mg, typically 1 ng to 100 mg, per milliliter. Single doses may contain, for example, 1 mg to 10 g of the active ingredient. Thus, ampoules for injections may contain, for example, from 1 mg to 100 mg, and orally administrable single-dose formulations, for example tablets or capsules, may contain, for example, from 1.0 to 1000 mg, typically from 10 to 600 mg. For prevention and/or treatment of the abovementioned conditions, the compounds of the formula I themselves may be used as the compound, but they are preferably present with a compatible carrier in the form of a pharmaceutical composition. The carrier must, of course, be acceptable in the sense that it is compatible with the other ingredients of the composition and is not harmful for the patient's health. The carrier may be a solid or a liquid or both and is preferably formulated with the compound as a single dose, for example as a tablet, which may contain 0.05% to 95% by weight of the active ingredient. Other pharmaceutically active substances may likewise be present, including other compounds of formula I. The pharmaceutical compositions of the invention can be produced by one of the known pharmaceutical methods, which essentially consist of mixing the ingredients with pharmacologically acceptable carriers and/or excipients.

Another subject of the present invention are processes for the preparation of the compounds of the formula I and their salts and solvates, by which the compounds are obtainable and which are outlined in the following.

ABBREVIATIONS

Abbreviations within this document have their common meanings unless defined otherwise herein. An exemplary list of abbreviations used, can be found below.

| Abbreviation | Meaning |
|---|---|
| Ac | acetyl |
| amu | atomic mass unit |
| atm | atmosphere (pressure unit, 101325 Pa) |
| BSA | bovine serum albumin |
| cAMP | cyclic adenosine monophosphate |

-continued

| Abbreviation | Meaning |
|---|---|
| cat. | catalyst/catalyzed |
| CDI | carbonyl diimidazole |
| dba | dibenzylideneacetone |
| DCM | dichloromethane |
| DEAD | diethyl azodicarboxylate |
| DIAD | diisopropyl azodicarboxylate |
| DIPEA | diisopropyl-ethyl-amine |
| DMEM | Dulbecco's modified eagle medium |
| DMF | dimethylformamide |
| DMSO | dimethylsulfoxide |
| dppf | diphenylphosphinoferrocene |
| EA | ethyl acetate |
| $EC_{50}$ | concentration causing 50% of the maximal response |
| EDCI | ethyl dimethylaminopropyl carbodiimide |
| ESI | electrospray ionization |
| FA | formic acid |
| FCS | fetal calf serum |
| GPR119 | G-protein coupled receptor 119 |
| h | hour(s) |
| Hal | halogen (atom) |
| HATU | O-(7-azabenzotriazol-1-yl)-N,N,N',N'-tetramethyl-uronium hexafluorophosphate |
| HBSS | Hank's buffered salt solution |
| HEK 293 | human embryonic kidney 293 |
| HEPES | 4-(2-hydroxyethyl)-1-piperazinyl-ethanesulfonic acid |
| HOBt | 1-hydroxy-benzotriazole |
| HPLC | high pressure liquid chromatography |
| HTRF | homogenous time-resolved fluorescence |
| IBMX | 1-methyl-3-(2-methylpropyl)-7H-purine-2,6-dione |
| LCMS | liquid chromatography coupled mass spectroscopy |
| LG | leaving group |
| MeCN | methyl cyanide (acetonitrile) |
| min | minute(s) |
| MS | mass spectroscopy |
| MTBE | methyl tert.-butyl ether |
| NMP | N-methyl pyrrolidin-2-one |
| NMR | nuclear magnetic resonance (spectrum) |
| PBS | phosphate buffered saline |
| PE | petroleum ether |
| PMBCl | para-methoxybenzyl chloride |
| $R_t$ | retention time |
| RT | room temperature |
| SGC | silica gel chromatography |
| $SiO_2$ | silica gel (for chromatography) |
| TBAF | tetra-n-butylammonium fluoride |
| TFA | trifluoroacetic acid |
| THF | tetrahydrofuran |
| TM | transition metal |
| TMS | tetramethylsilane |
| $TMSCHN_2$ | trimethylsilyldiazomethane |
| Ts | para-tolylsulfonyl |
| UV | ultraviolet (spectrum) |

Synthetic Methods

Variables in the formulae of the schemes represent moieties as defined above unless other meanings are given.

Detailed descriptions of the Typical Procedures to which reference is made in this section can be found in the Examples section.

Compounds of the invention having the formula I may be prepared by combining known synthetic procedures. In a first method 3-hydroxy-pyrrolidin-2-one (A') (commercially available as racemic mixture and in both enantiomeric forms) is coupled with aryl halides B' (typically Hal is Br or I) to provide intermediates C. An example for suitable coupling conditions (CuI, N,N-dimethyl-ethane-1,2-diamine, cesium carbonate) can be found in the Typical Procedure 1. Conversion of the hydroxy group in C to a suitable leaving group (LG is for example Br, I, OTs or $OPPh_3^+$) can be accomplished with various well known reagents (e.g. $PPh_3/I_2$, $PPh_3/CBr_4$, $PPh_3/DIAD$ or $TsCl/NEt_3$) providing the intermediates D, which may be isolated or may be reacted without isolation with hydroxy-aryl building blocks of type E' using an appropriate base (e.g. Na$_2$CO$_3$, K$_2$CO$_3$, Cs$_2$CO$_3$ or NaH). For example the conditions in the Typical Procedure 3 may be applied to couple intermediates C and E to provide compounds I.

A second method of synthesizing compounds I starts with a pyrrolidin-2-one substituted with a leaving group (LG) in 3-position (structures F), which may be prepared by reacting A' with the reagents mentioned above. Other procedures for making structures F are known (e.g. base-promoted cyclization of 2,4-dibromo-butyramide). Intermediates F may be isolated or generated in situ to react with hydroxy-aryls E' (typically in the presence of a base as described above) to provide intermediates G'. As a final step, for example copper-catalyzed coupling with aryl halides B' provides the desired compounds I (Scheme 1).

Aryl halides B' are either commercial or obtained by known synthetic procedures. For example 6-bromo-2H-1,2,4-triazolo[4,3-a]pyridin-3-ones (intermediates B' in which Hal=Br; G, E, A=N; B=CO) can be made by cyclization reaction of eventually substituted (5-bromo-pyridin-2-yl)-hydrazines, obtained for example from 5-bromo-2-halo-pyridines and hydrazine, with phosgene or phosgene equivalents like CDI. Alkylation, for example with R30-LG, gives access to further intermediates B' (Hal=Br; G, E, A=N; B=CO) as illustrated in Scheme 2.

27
-continued

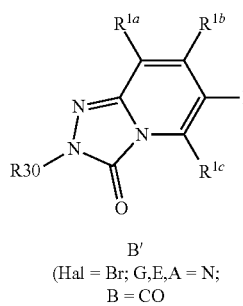

(Hal = Br; G,E,A = N;
B = CO)

Certain compounds I (Y=N; Z=O, S, NR6) may be prepared by coupling aryl halides B' with hydroxy-pyridines E' (Y=N; Z=O, S, NR6). Said hydroxy-pyridines E' may be prepared by displacement of a halide (F, Cl, Br or I) in the 2-position of 5-bromo-2-halo-pyridines, which are substituted with $R^{2a}$, $R^{2b}$ and $R^{2c}$, using nucleophiles of the type HZ—$R^3$—$R^4$ (Z=O, S, NR6) followed by conversion of the 5-bromo-substituent to a hydroxy group (e.g. by oxidation of a boronate group introduced by palladium catalyzed coupling with bis-pinacolato-diboron). See Typical Procedure 6 for exemplary conditions for the nucleophilic displacement reaction, Typical Procedure 5 for an example of boronate-oxidation conditions, Typical Procedure 4 for an example of conditions to install a boronate group and Scheme 3 for illustration of the overall method.

A benzyl group ($R^3$-$R^4$=$CH_2$-Ph) in compounds I (Y=N, Z=O, S) may be cleaved for example by hydrogenolysis to provide intermediates J, which may be alkylated by LG-$R^{3'}$—$R^{4'}$, $R^{3'}$ and $R^{4'}$ being defined like $R^3$ and $R^4$, respectively, to yield compounds I (Y=N; Z=O, S).

For example, the structure J may be a 2-hydroxy-pyridine (Z=O), which may be alkylated under Mitsunobu-conditions ($PPh_3$/DIAD; see for example Typical Procedure 3) starting with alcohols HO—$R^{3'}$—$R^{4'}$. Triphenylphosphine may be introduced into the reaction as polymer. DIAD may be replaced by other azodicarboxylates (e.g. DEAD).

Scheme 3.

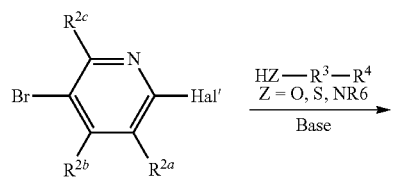

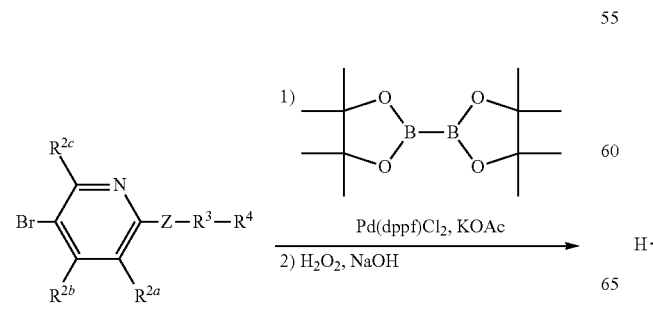

28
-continued

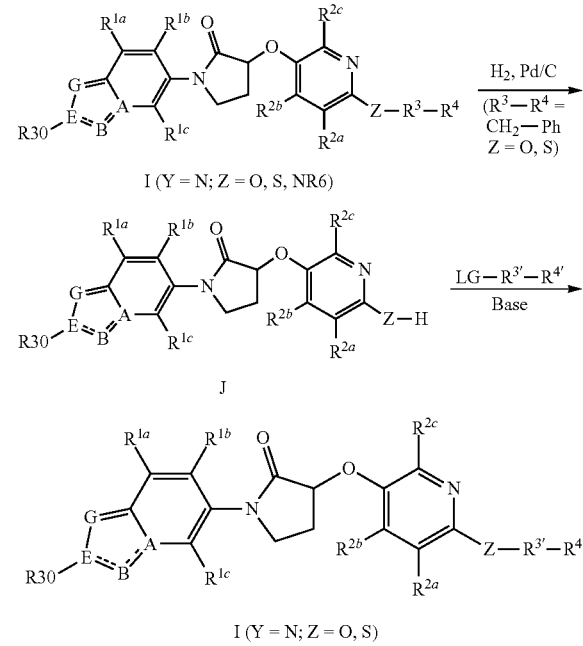

Certain other compounds of the invention may be prepared by reaction of hydroxy-pyrrolidinones C with 6-bromo-pyridin-3-ols under Mitsunobu-conditions and subsequent transition metal catalyzed replacement of the Br-atom by Z—$R^3$-$R^4$.

Variation of the order of the steps in the synthetic sequence provides further methods to prepare compounds I. For example intermediates F may be reacted with 6-bromo-pyridin-3-ols and subsequently the bromo-substituent may be exchanged for Z—$R^3$—$R^4$ to provide intermediates G' (Y=N). In a last step, coupling with aryl halides B' again provides compounds I (Y=N) as illustrated in Scheme 4.

Scheme 4.

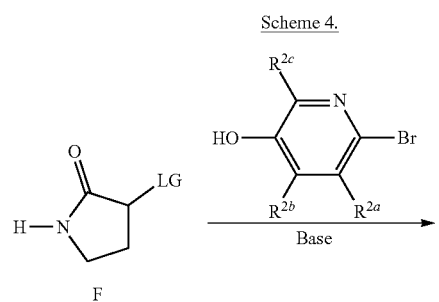

-continued

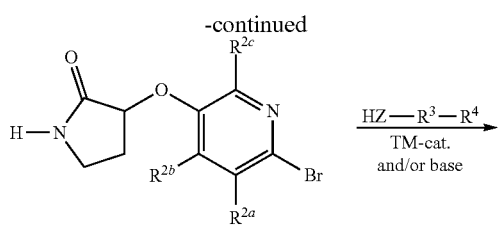

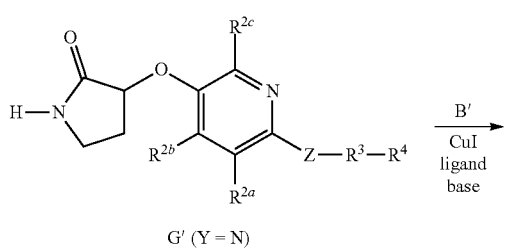

G' (Y = N)

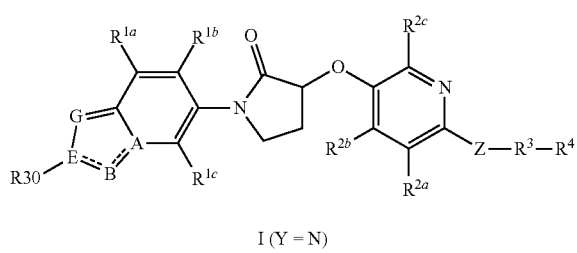

I (Y = N)

Other compounds of formula I (e.g. with R30=CH$_2$COOH) can be obtained by cleaving the ester functionality in structures I (R30=CH$_2$COO(C$_1$-C$_6$)-alkyl). Still other compounds I (R30=CH$_2$CONR14R15) are provided by the reaction of said acids with amines of the structure HNR14R15 using for example EDCl as coupling reagent (see Typical Procedure 7 for exemplary conditions).

Analytical Methods

Examples were characterized by standard analytical methods. This includes at least two methods (e.g. selected from HPLC, MS, $^1$H-NMR). In particular, MS and HPLC data were obtained by combined analytical HPLC/MS (LCMS). For example the following LCMS methods were used.

Method A

Column: Waters UPLC BEH C18 2.1*50 mm, 1.7 µm; mobile phase: (H$_2$O+0.05% FA): (MeCN+0.035% FA) 98:2 (0 min) to 5:95 (2 min) to 5:95 (2.6 min) to 95:5 (2.7 min) to 95:5 (3 min); flow rate: 0.9 mL/min; temperature: 55° C.; ionization method: ES$^+$; UV wavelength: 220 nm.

Method B

Column: Waters UPLC BEH C18 2.1*50 mm, 1.7 µm; mobile phase: (H$_2$O+0.05% FA): (MeCN+0.035% FA) 95:5 (0 min) to 5:95 (2 min) to 5:95 (2.6 min) to 95:5 (2.7 min) to 95:5 (3 min); flow rate: 0.9 mL/min; temperature: 55° C.; ionization method: ES$^+$; UV wavelength: 220 nm.

Method C

Column: Waters XBridge C18 4.6*50 mm, 2.5 µm, mobile phase: (H$_2$O+0.1% FA) (MeCN+0.1% FA) 97:3 (0 min) to 40:60 (3.5 min) to 2:98 (4 min) to 2:98 (5 min) to 97:3 (5.2 min) to 97:3 (6.5 min); flow rate: 0.9 mL/min; temperature: 55° C.; ionization method: ES$^+$; UV wavelength: 220 nm.

In general, HPLC data is represented by the retention time (R$_t$; in min); MS data is given as the observed mass number (m/z) of the ion [M+H]$^+$ (if present) and $^1$H-NMR data is reported by lists of chemical shifts δ (in ppm vs. TMS) of the observed signals (the number of hydrogen atoms was determined using the area under the respective signal; signal multiplicity is characterized as follows: s=singlet, d=doublet, dd=doublet of doublets, t=triplet, dt=doublet of triplets, q=quartet, m=multiplet, br=broad; coupling constants J are given in Hertz (Hz)). Deuterated solvents were used for NMR spectroscopy.

EXAMPLES

The following examples are particular embodiments of the invention. They partially illustrate the scope of the invention without limiting it.

Abbreviations and chemical symbols have their usual and customary meanings unless otherwise indicated.

The examples were prepared, isolated and analyzed by the procedures and methods given. Alternatively they may be prepared by the general synthetic methods detailed above. Further variations of the synthetic procedures may be proposed by a person skilled in the art.

When example compounds containing a basic group were purified by preparative HPLC on reversed phase column material and, as customary, the eluent was a gradient mixture of water and acetonitrile containing trifluoroacetic acid (TFA), they were obtained in part in the form of their addition salt with TFA, depending on the details of the workup such as evaporation or lyophilization conditions. In the names of the example compounds and their structural formulae any such TFA present is not specified.

Preparation of Examples 1

Example 1-01 (Typical Procedure 1)

To a mixture of 6-bromo-2-cyclopropyl-[1, 2, 4]triazolo[1,5-a]pyridine (77 mg), (R)-3-((6-(cyclopropylmethoxy)pyridin-3-yl)oxy)pyrrolidin-2-one (80 mg) and 1,4-dioxane (1 mL) was added N,N'-dimethyl-ethane-1,2-diamine (243 µL) and cesium carbonate (262 mg). The mixture was purged for 5 minutes with a flow of argon and CuI (4.3 mg) was added. The mixture was heated at 80° C. for 30 minutes. After cooling to RT insoluble material was removed by filtration and the filtrate concentrated. The residue was purified by preparative HPLC to provide example 1-01.

Following essentially the Typical Procedure 1, the Examples 1 in Table 1 were prepared using the respective aryl bromides and 3-substituted pyrrolidinones.

TABLE 1

| Example | Structure | LCMS Method | R$_t$ [min] | ESI$^+$ m/z [amu] |
|---|---|---|---|---|
| 1-01 | 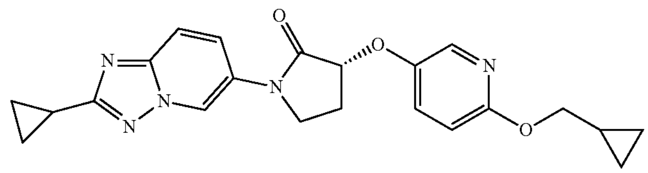 [SMILES: O=C1[C@H](Oc2ccc(OCC3CC3)nc2)CCN1c1ccc2nc(C3CC3)nn2c1] | A | 1.78 | 406.4 |
| 1-02 | 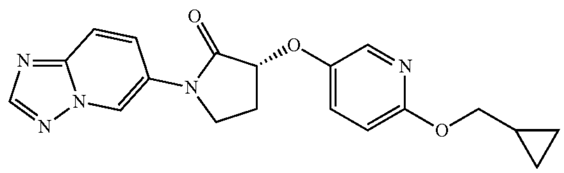 [SMILES: O=C1[C@H](Oc2ccc(OCC3CC3)nc2)CCN1c1ccc2ncnn2c1] | A | 1.51 | 366.1 |
| 1-03 | 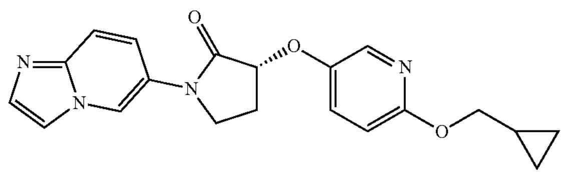 [SMILES: O=C1[C@H](Oc2ccc(OCC3CC3)nc2)CCN1c1ccc2nccn2c1] | A | 1.22 | 365.1 |
| 1-04 | 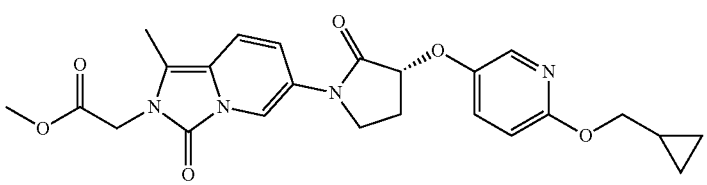 [SMILES: COC(=O)Cn1c(C)c2ccc(N3CC[C@@H](Oc4ccc(OCC5CC5)nc4)C3=O)cn2c1=O] | A | 1.67 | 467.3 |
| 1-05 | 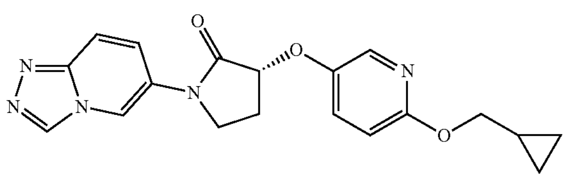 [SMILES: O=C1[C@H](Oc2ccc(OCC3CC3)nc2)CCN1c1ccc2nncn2c1] | A | 1.42 | 366.1 |
| 1-06 | 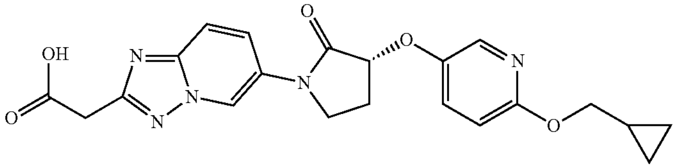 [SMILES: O=C(O)Cc1nc2ccc(N3CC[C@@H](Oc4ccc(OCC5CC5)nc4)C3=O)cn2n1] | A | 1.60 | 424.4 |
| 1-07 | 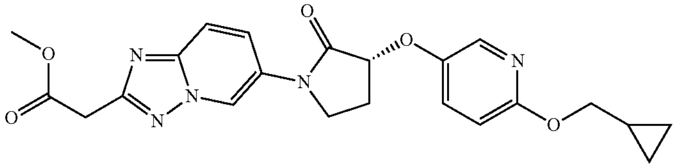 [SMILES: COC(=O)Cc1nc2ccc(N3CC[C@@H](Oc4ccc(OCC5CC5)nc4)C3=O)cn2n1] | A | 1.73 | 438.3 |
| 1-08 | 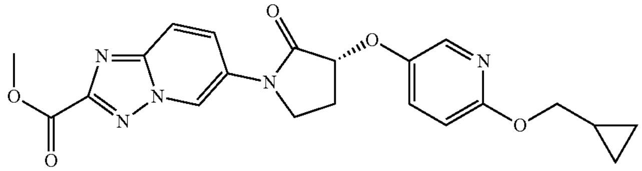 [SMILES: COC(=O)c1nc2ccc(N3CC[C@@H](Oc4ccc(OCC5CC5)nc4)C3=O)cn2n1] | A | 1.74 | 424.3 |

TABLE 1-continued

| Example | Structure | LCMS Method | R$_t$ [min] | ESI$^+$ m/z [amu] |
|---|---|---|---|---|
| 1-09 | 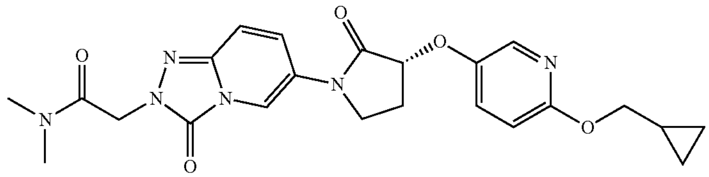 [SMILES: CN(C)C(=O)Cn1nc2ccc(N3CC[C@@H](Oc4ccc(OCC5CC5)nc4)C3=O)cn2c1=O] | A | 1.52 | 467.5 |
| 1-10 | 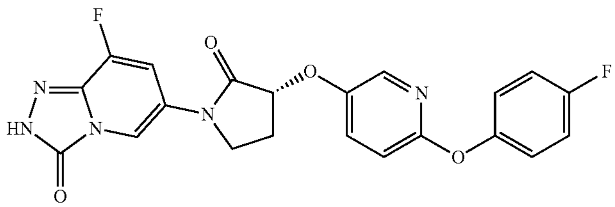 [SMILES: O=C1[C@H](Oc2ccc(Oc3ccc(F)cc3)nc2)CCN1c1cc(F)c2n[nH]c(=O)n2c1] | A | 1.64 | 440.1 |
| 1-11 | 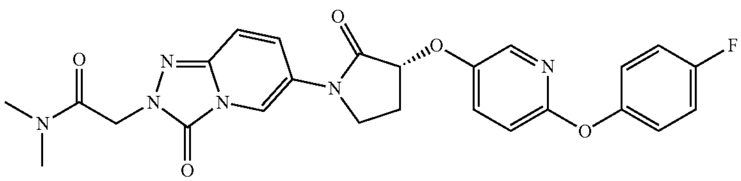 [SMILES: CN(C)C(=O)Cn1nc2ccc(N3CC[C@@H](Oc4ccc(Oc5ccc(F)cc5)nc4)C3=O)cn2c1=O] | A | 1.59 | 507.2 |
| 1-12 | 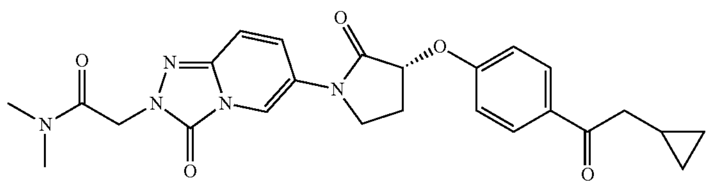 [SMILES: CN(C)C(=O)Cn1nc2ccc(N3CC[C@@H](Oc4ccc(C(=O)CC5CC5)cc4)C3=O)cn2c1=O] | B | 1.72 | 478.2 |
| 1-13 | 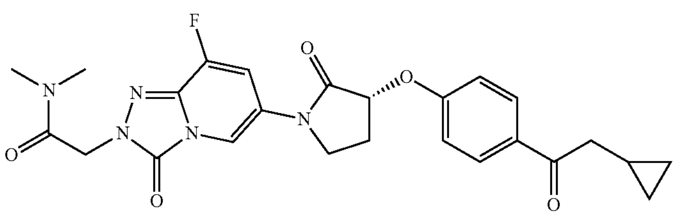 [SMILES: CN(C)C(=O)Cn1nc2c(F)cc(N3CC[C@@H](Oc4ccc(C(=O)CC5CC5)cc4)C3=O)cn2c1=O] | B | 1.78 | 496.1 |
| 1-14 | 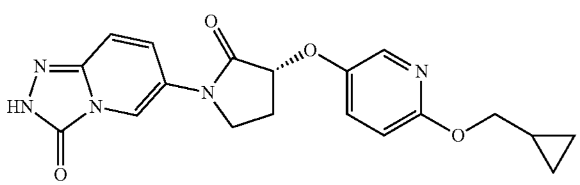 [SMILES: O=C1[C@H](Oc2ccc(OCC3CC3)nc2)CCN1c1ccc2n[nH]c(=O)n2c1] | B | 1.49 | 382.1 |
| 1-15 | 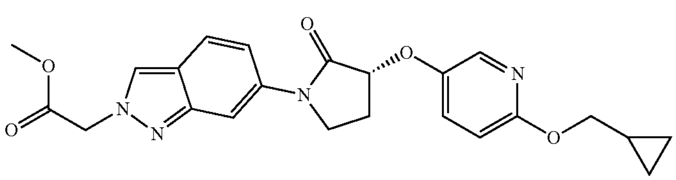 [SMILES: COC(=O)Cn1cc2ccc(N3CC[C@@H](Oc4ccc(OCC5CC5)nc4)C3=O)cc2n1] | A | 1.69 | 437.2 |
| 1-16 | 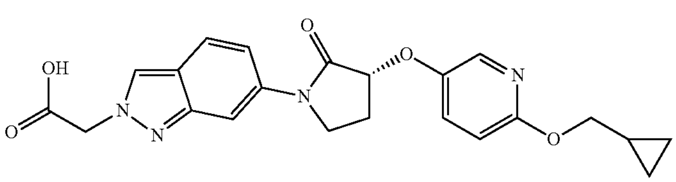 [SMILES: O=C(O)Cn1cc2ccc(N3CC[C@@H](Oc4ccc(OCC5CC5)nc4)C3=O)cc2n1] | A | 1.59 | 423.2 |

TABLE 1-continued

| Example | Structure | LCMS Method | R$_t$ [min] | ESI$^+$ m/z [amu] |
|---|---|---|---|---|
| 1-17 | 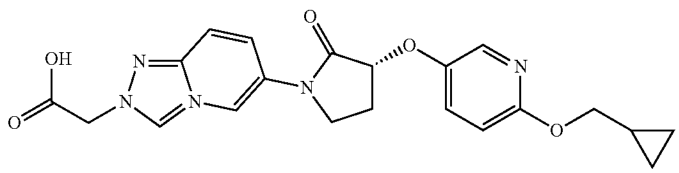 | A | 1.56 | 424.2 |
| 1-18 | 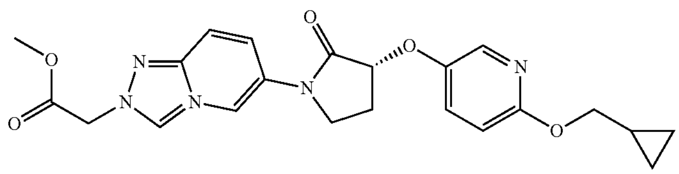 | A | 1.72 | 438.3 |
| 1-19 | 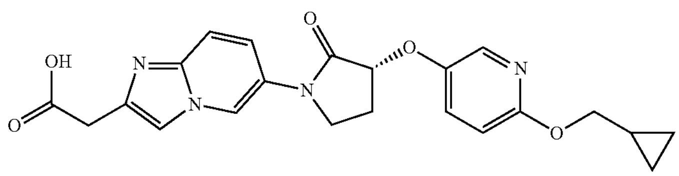 [SMILES: O=C(O)Cc1cn2cc(N3CC[C@@H](Oc4ccc(OCC5CC5)nc4)C3=O)ccc2n1] | C | 2.86 | 423.2 |
| 1-20 | 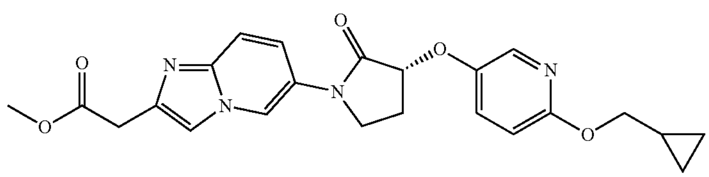 [SMILES: COC(=O)Cc1cn2cc(N3CC[C@@H](Oc4ccc(OCC5CC5)nc4)C3=O)ccc2n1] | A | 1.33 | 437.3 |
| 1-21 | 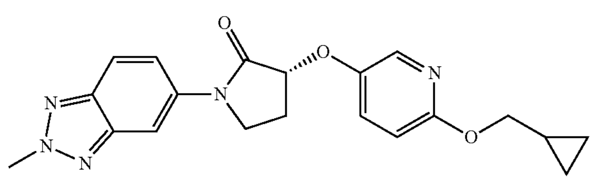 [SMILES: Cn1nc2ccc(N3CC[C@@H](Oc4ccc(OCC5CC5)nc4)C3=O)cc2n1] | A | 1.70 | 380.3 |
| 1-22 | 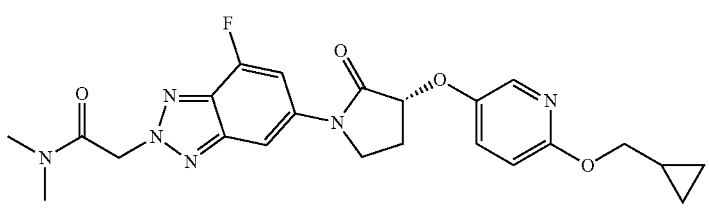 [SMILES: CN(C)C(=O)Cn1nc2cc(N3CC[C@@H](Oc4ccc(OCC5CC5)nc4)C3=O)cc(F)c2n1] | A | 1.68 | 469.2 |
| 1-23 | 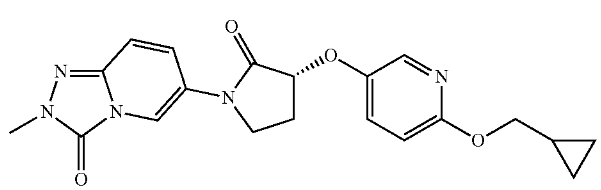 [SMILES: Cn1nc2ccc(N3CC[C@@H](Oc4ccc(OCC5CC5)nc4)C3=O)cn2c1=O] | A | 1.50 | 396.2 |
| 1-24 | 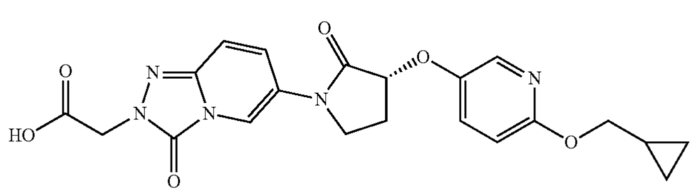 [SMILES: O=C(O)Cn1nc2ccc(N3CC[C@@H](Oc4ccc(OCC5CC5)nc4)C3=O)cn2c1=O] | A | 1.45 | 440.2 |

TABLE 1-continued

| Example | Structure | LCMS Method | R$_t$ [min] | ESI$^+$ m/z [amu] |
|---|---|---|---|---|
| 1-25 | 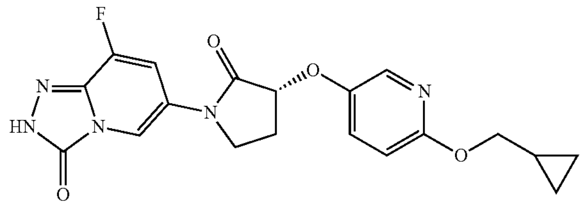 [SMILES: O=C1[C@H](Oc2ccc(OCC3CC3)nc2)CCN1c1cc(F)c2n[nH]c(=O)n2c1] | A | 1.52 | 400.2 |
| 1-26 | 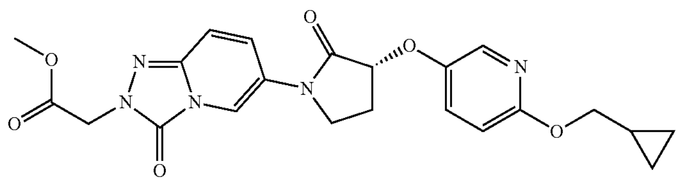 [SMILES: COC(=O)Cn1nc2ccc(N3CC[C@@H](Oc4ccc(OCC5CC5)nc4)C3=O)cn2c1=O] | A | 1.56 | 454.2 |
| 1-27 | 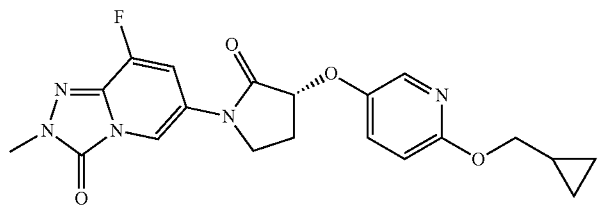 [SMILES: Cn1nc2c(F)cc(N3CC[C@@H](Oc4ccc(OCC5CC5)nc4)C3=O)cn2c1=O] | A | 1.67 | 414.2 |
| 1-28 | 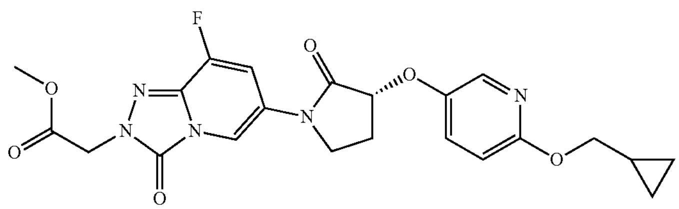 [SMILES: COC(=O)Cn1nc2c(F)cc(N3CC[C@@H](Oc4ccc(OCC5CC5)nc4)C3=O)cn2c1=O] | A | 1.64 | 472.1 |
| 1-29 | 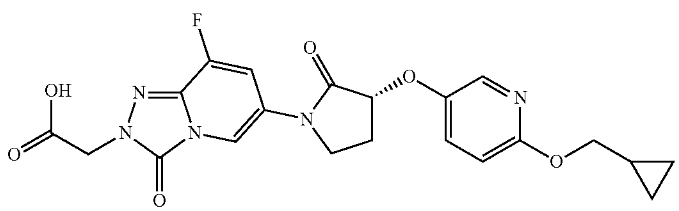 [SMILES: O=C(O)Cn1nc2c(F)cc(N3CC[C@@H](Oc4ccc(OCC5CC5)nc4)C3=O)cn2c1=O] | A | 1.53 | 458.1 |
| 1-30 | 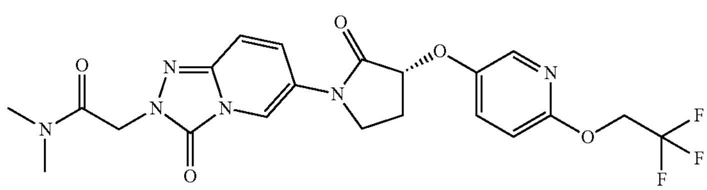 [SMILES: CN(C)C(=O)Cn1nc2ccc(N3CC[C@@H](Oc4ccc(OCC(F)(F)F)nc4)C3=O)cn2c1=O] | B | 1.56 | 495.1 |
| 1-31 | 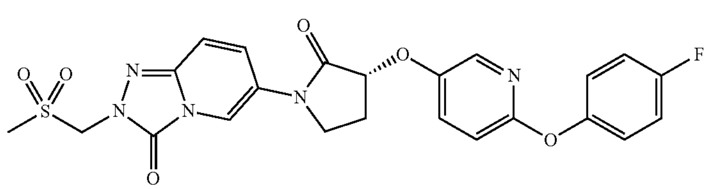 [SMILES: CS(=O)(=O)Cn1nc2ccc(N3CC[C@@H](Oc4ccc(Oc5ccc(F)cc5)nc4)C3=O)cn2c1=O] | B | 1.57 | 514.1 |

TABLE 1-continued

| Example | Structure | LCMS Method | R$_t$ [min] | ESI$^+$ m/z [amu] |
|---|---|---|---|---|
| 1-32 | (chemical structure) | B | 1.46 | 471.1 |
| 1-33 | (chemical structure) | B | 1.57 | 502.1 |
| 1-34 | (chemical structure) | B | 1.61 | 478.3 |

Occasionally carboxylic acids (e.g. Examples 1-06, 1-16, 1-17, 1-19, 1-24 and 1-29 respectively) were obtained as additional products from the reaction mixture due to (partial) ester hydrolysis (for example in the reaction of methyl 2-(6-bromo-[1,2,4]triazolo[1,5-a]pyridin-2-yl)acetate, methyl 6-bromo-[1,2,4]triazolo[1,5-a]pyridine-2-carboxylate, methyl 2-(6-bromo-8-fluoro-3-oxo-[1,2,4]triazolo[4,3-a]pyridin-2(3H)-yl)acetate, methyl 2-(6-bromo-2H-indazol-2-yl)acetate, methyl 2-(5-bromo-2H-benzo[d][1,2,3]triazol-2-yl)acetate, ethyl 2-(6-bromoimidazo[1,2-a]pyridin-2-yl)acetate, methyl 2-(6-bromo-3-oxo-[1,2,4]triazolo[4,3-a]pyridin-2(3H)-yl)acetate and methyl 2-(6-bromo-8-fluoro-3-oxo-[1,2,4]triazolo[4,3-a]pyridin-2(3H)-yl)acetate, respectively, with (R)-3-[6-(2-cyclopropyl-methoxy)-pyridin-3-yloxy]-pyrrolidin-2-one according to Typical Procedure 1). The carboxylic acids obtained can be converted to methyl esters (e.g. Examples 1-07, 1-08, 1-15, 1-18, 1-20, 1-26 and 1-28 respectively) by dissolving the respective acid in DCM (5 mL/mmol) and methanol (0.5 mL/mmol) and addition of TMSCHN$_2$ (1.5 equiv.). After the gas evolution has ceased, the reaction mixture is evaporated to provide the desired methyl ester (Typical Procedure 2).

Preparation of 3-Substituted Pyrrolidin-2-ones (R)-3-[6-(4-Fluoro-phenoxy)-pyridin-3-yloxy]-pyrrolidin-2-one (Typical Procedure 3)

A mixture of THF (200 mL) and DCM (100 mL) under argon was added triphenylphosphine (polymer, 1.8 mmol/g, 20 g). DIAD (8.87 g) was added. After 5 minutes (S)-3-hydroxy-pyrrolidin-2-one (3.1 g) and 6-(4-fluoro-phenoxy)-pyridin-3-ol (6.0 g) were added. After 30 minutes the mixture was filtered and the filtrate concentrated. The residue was purified by chromatography (SiO$_2$; DCM/MeOH 15:1) to provide the title compound. MS ESI$^+$: m/z=289 [M+H]$^+$.

6-(4-Fluoro-phenoxy)-pyridin-3-ol

A mixture of 6-bromo-pyridin-3-ol (8.0 g), 4-fluorophenol (15.5 g) and cesium carbonate (30 g) was heated to 170° C. for 6 hours. After the mixture reached room temperature, it was distributed between water and MTBE. The organic phase was dried (Na$_2$SO$_4$) and concentrated. The residue was purified by chromatography (SiO$_2$; EA/heptane 1:1.5) to provide the subtitle compound. MS ESI$^+$: m/z=206 [M+H]$^+$.

(R)-3-[6-(2-Cyclopropyl-methoxy)-pyridin-3-yloxy]-pyrrolidin-2-one

To a mixture of (S)-3-hydroxy-pyrrolidin-2-one (3.00 g), 6-(2-cyclopropyl-methoxy)-pyridin-3-ol (4.90 g), triphenylphosphine (polymer, 8.56 g), DCM (30 mL) and THF (50 mL) was added DIAD (6.60 g) keeping the reaction temperature below 30° C. After 12 hours the mixture was filtered and the filtrate was evaporated. The residue was purified by SGC (eluent: EA/MeOH 9:1) to provide the title compound. MS ESI$^+$: m/z=249 [M+H]$^+$.

6-Cyclopropylmethoxy-pyridin-3-ol ((Typical Procedure 4)

A mixture of 5-bromo-2-cyclopropylmethoxy-pyridine (8.00 g), bis(pinacolato)diboron (8.91 g) and 1,4-dioxane (53 mL) was purged with argon. Potassium acetate (3.44 g) and Pd(dppf)Cl$_2$ (2.57 g) were added and the mixture heated to 100° C. for 1 hour by microwave irradiation. The mixture was filtered and the filtrate diluted with EA, washed with water, dried (Na$_2$SO$_4$) and concentrated. The residue was purified by SGC (eluent: EA/heptane 1:6) to provide the crude boronate. MS ESI$^+$: m/z=276 [M+H]$^+$.

Typical Procedure 5

The boronate from above was dissolved in THF (60 mL). Aqueous NaOH (5 M) was added at 0° C. Hydrogen peroxide (30% in water, 30 mL) was added slowly. The mixture was allowed to warm to RT and stirred for 4 hours. The mixture was extracted with MTBE. The aqueous phase was adjusted to pH 3-4 by addition of diluted HCl and extracted with EA. The organic phase was dried (Na$_2$SO$_4$) and concentrated to provide the subtitle compound. MS ESI$^+$: m/z=166 [M+H]$^+$.

5-Bromo-2-cyclopropylmethoxy-pyridine (Typical Procedure 6)

To a mixture of 2-cyclopropyl-methanol (6.15 g) and DMF (12 mL) was added NaH (60% in mineral oil, 1.5 g) at 0° C. After stirring for 4 hours at RT the mixture was diluted with DMF (5 mL) and 5-bromo-2-fluoro-pyridine (6.00 g) was slowly added keeping the reaction temperature below 30° C. After 30 minutes at RT the mixture was heated to 130° C. for 1 hour by microwave irradiation. After cooling to RT the mixture was diluted with EA and washed with water (3x). The organic phase was dried (Na$_2$SO$_4$) and concentrated. The residue was purified by SGC to provide the subtitle compound. MS ESI$^+$: m/z=228 [M+H]$^+$.

(R)-3-(4-(2-Cyclopropylacetyl)phenoxy)pyrrolidin-2-one

A solution of 2-cyclopropyl-1-(4-hydroxyphenyl)ethanone (1.1 g), (S)-3-hydroxypyrrolidin-2-one (947 mg), PPh$_3$ (2.78 g) and DIAD (2.15 g) in THF (5 mL) was stirred at 4° C. for 15 hours. The reaction mixture was diluted with EA (200 mL), and washed with water (100 mL×2) and brine (100 mL). The organic layer was dried over anhydrous Na$_2$SO$_4$, filtered and concentrated. The residue was purified by column chromatography on silica gel eluting with DCM/MeOH=50:1 to provide the title compound. MS ESI$^+$: m/z=260 [M+H]$^+$.

2-Cyclopropyl-1-(4-hydroxyphenyl)ethanone

To a solution of 1-(4-(tert-butyldimethylsilyloxy)phenyl)-2-cyclopropylethanone (3.8 g) in THF (50 mL) was added a solution of TBAF (6.65 g) in THF (10 mL). The reaction mixture was stirred for 4 hours at RT. The solvent was removed under reduced pressure and the residue was dissolved in EA (100 mL), washed with HCl (0.5 N, 20 mL), brine (20 mL) and dried over Na$_2$SO$_4$. The residue was purified by column chromatography on silica gel eluting with DCM/MeOH=200:1 to provide the subtitle compound. MS ESI$^+$: m/z=177 [M+H]$^+$.

1-(4-(Tert-butyldimethylsilyloxy)phenyl)-2-cyclopropylethanone

To a solution of (4-bromophenoxy)(tert-butyl)dimethylsilane (3.15 g) in THF (20 mL) was added a solution of t-BuLi (6.8 mL, 10.9 mmol) dropwise at −78° C. The reaction mixture was stirred for 20 min at −78° C. and then a solution of 2-cyclopropyl-N-methoxy-N-methylacetamide (1.3 g) in dry THF (5 mL) was added slowly. The reaction mixture was warm to RT and stirred for 4 hours. The reaction mixture was poured into water (100 mL) and the volatiles were removed under reduced pressure. The aqueous phase was extracted with EA (50 mL×3). The organic phase was washed with brine and dried over Na$_2$SO$_4$. After filtration, the solvent was removed under reduced pressure to provide the subtitle compound. MS ESI$^+$: m/z=291 [M+H]$^+$.

(4-Bromophenoxy)(tert-butyl)dimethylsilane

To a solution of 4-bromophenol (5 g) in DMF (25 mL) was added tert-butylchlorodimethylsilane (5 g) and imidazole (5 g) in portions at RT. The mixture was stirred for 3 hours and then poured into water (200 mL). The mixture was extracted with Et$_2$O (80 mL×3). The organic phase was washed with water (30 mL×4), HCl (1 N, 30 mL), saturated NaHCO$_3$ (30 mL) and brine (30 mL). The organic phase was dried over Na$_2$SO$_4$. After filtration, the solvent was removed under reduced pressure to provide the subtitle compound.

2-Cyclopropyl-N-methoxy-N-methylacetamide

To a stirred solution of 2-cyclopropylacetic acid (1 g) in DCM (30 mL) was added CDI (1.86 g) at room temperature. The mixture was stirred for 2 hours at RT and then O,N-dimethylhydroxylamine hydrochloride (1.07 g) was added. The reaction mixture was stirred for 20 hours at RT The reaction mixture was poured into water (100 mL) and then extracted with DCM (30 mL×3). The organic phase was washed with water (50 mL), HCl (1 N, 30 mL), saturated NaHCO$_3$ (30 mL) and dried over Na$_2$SO$_4$. After filtration the solvent was removed under reduced pressure to provide the subtitle compound.

(R)-3-[6-(2,2,2-Trifluoro-ethoxy)-pyridin-3-yloxy]-pyrrolidin-2-one

Following Typical Procedure 3, reaction of 6-(2,2,2-trifluoroethoxy)pyridin-3-ol with (S)-3-hydroxy-pyrrolidin-2-one provided the title compound. MS ESI$^+$: m/z=277 [M+H]$^+$.

6-(2,2,2-Trifluoroethoxy)pyridin-3-ol

Following Typical Procedures 4 and 5, conversion of 5-bromo-2-(2,2,2-trifluoroethoxy) pyridine to the boronate and oxidation provided the subtitle compound. MS ESI$^+$: m/z=194 [M+H]$^+$.

5-Bromo-2-(2, 2, 2-trifluoroethoxy) pyridine

Following Typical Procedure 6, reaction of 5-bromo-2-fluoro-pyridine with 2,2,2-trifluoroethanol provided the subtitle compound. MS ESI$^+$: m/z=256 [M+H]$^+$.

Preparation of Aryl Bromides

6-Bromo-2-cyclopropyl-[1, 2, 4]triazolo[1,5-a]pyridine

A mixture of 5-bromo-1,2-diamino-pyridinium 2,4,6-trimethyl-benzenesulfonate (3.0 g) and cyclopropylcarbonyl chloride (1.6 g) in pyridine (20 mL) was stirred at 100° C. for 5 hours. After cooling, the solvent was evaporated and the orange residue dissolved in water (40 mL) and extracted with ethyl acetate (50 mL×3). The organic extracts were washed with brine and dried over Na$_2$SO$_4$. After filtration and evaporation of the solvent, the resulting residue was purified on column chromatography (silica gel, PE:EA=5:1) to provide the title compound. MS ESI+: m/z=238 [M+H]+.

5-Bromo-1,2-diamino-pyridinium 2,4,6-trimethyl-benzenesulfonate

A solution of O-mesitylsulfonyl-hydroxylamine (6.33 g) in CHCl$_3$ (200 mL) was cooled to 0° C. 5-Bromo-pyridin-2-ylamine (9.0 g) was added and the mixture was stirred at RT for 3 hours. After the reaction was completed, the precipitate was isolated by filtration, and dried under vacuum.

Methyl 2-(6-bromo-1-methyl-3-oxoimidazo[1,5-a]pyridin-2(3H)-yl)acetate

To a solution of methyl 2-(1-(5-bromopyridin-2-yl)ethylamino)acetate (2.9 g) and N,N-diethylbenzenamine (5.86 g) in toluene (50 mL) was added triphosgene (4.72 g) in portions at 0° C. The suspension was warmed to RT and stirred for 2 hours and then the mixture was quenched with water (150 mL) and extracted with EA (50 mL×3). The combined organic phases were washed with brine and dried over Na$_2$SO$_4$. After filtration, the solvent was removed under reduced pressure and the residue was purified by column chromatography on silica gel eluting with DCM/MeOH=99:1 to provide the title compound. MS ESI+: m/z=299 [M+H]+.

Methyl 2-(1-(5-bromopyridin-2-yl)ethylamino)acetate

To a solution of 1-(5-bromopyridin-2-yl)ethanamine (3 g) in DMF (20 mL) was added K$_2$CO$_3$ (2.1 g) and methyl 2-bromoacetate (2.3 g) at RT and the suspension was stirred for 3 hours and then the mixture was poured into water (100 mL). The aqueous phase was extracted with EA (40 mL×3). The combined organic phases were washed with brine and dried over Na$_2$SO$_4$. After filtration, the solvent was removed under reduced pressure and the residue was purified by column chromatography on silica gel eluting with DCM/MeOH=99:1 to provide the subtitle compound. MS ESI+: m/z=273 [M+H]+.

1-(5-Bromopyridin-2-yl)ethanamine

To a stirred solution of 5-bromopicolinonitrile (10 g) in dry THF (150 mL) was added methylmagnesium bromide (20 mL, 3 M in THF) at −20° C. After addition, the mixture was allowed to warm to RT with stirring for 30 minutes. The reaction mixture was then treated with MeOH (200 mL) and NaBH$_4$ (4 g). The reaction was stirred at RT for 15 hours and then poured into a solution of NaOH in water (200 mL, 1 M). The organic solvent was removed under reduced pressure and the aqueous phase was extracted with EA (100 mL×3). The combined organic phase was washed with brine (50 mL) and dried over Na$_2$SO$_4$. After filtration, the solvent was removed under reduced pressure and the residue was purified by column chromatography on silica gel eluting with DCM/MeOH=99:1 to provide the subtitle compound. MS ESI+: m/z=201 [M+H]+.

Methyl 2-(6-bromo-[1,2,4]triazolo[1,5-a]pyridin-2-yl)acetate

A mixture of 5-bromo-1,2-diamino-pyridinium 2,4,6-trimethyl-benzenesulfonate (2.8 g) and chlorocarbonyl-acetic acid methyl ester (2.2 g) in pyridine (25 mL) was stirred at 100° C. for 5 hours. After cooling, the volatiles were removed. The orange residue was dissolved in water (50 mL) and extracted with ethyl acetate (50 mL×3). The organic extracts were washed with brine and dried over Na$_2$SO$_4$. After filtration and evaporation of the solvent, the resulting residue was purified by column chromatography (silica gel, PE/EA=5:1) to provide the title compound. MS ESI+: m/z=270 [M+H]+.

Methyl 6-bromo-[1,2,4]triazolo[1,5-a]pyridine-2-carboxylate

To a solution of 5-bromo-1,2-diamino-pyridinium 2,4,6-trimethyl-benzenesulfonate (3.0 g) in pyridine (30 mL) was added chloro-oxo-acetic acid methyl ester (1.9 g). The mixture was stirred at 100° C. for 5 hours. After cooling, the volatiles were removed in vacuo and the orange residue dissolved in water (50 mL) and extracted with ethyl acetate (50 mL×3). The organic extracts were washed with brine and dried over Na$_2$SO$_4$. After filtration and evaporation of the solvent, the resulting residue was purified by column chromatography (silica gel, PE/EA=4:1) to provide the title compound. MS ESI+: m/z=256 [M+H]+.

2-(6-Bromo-3-oxo-[1,2,4]triazolo[4,3-a]pyridin-2(3H)-yl)-N,N-dimethylacetamide

To a mixture of 6-bromo-[1,2,4]triazolo[4,3-a]pyridin-3(2H)-one (1.0 g), cesium carbonate (3.0 g) and DMF (10 mL) was added 2-bromo-N,N-dimethyl-acetamide (776 mg). After 12 hours the reaction mixture was partitioned between water and EA. The aqueous phase was extracted with EA. The combined organic phases were washed with brine, dried over Na$_2$SO$_4$ and evaporated. The residue was slurried with methanol (2 mL) and acetone (10 mL). The resulting precipitate was isolated by filtration to provide the title compound. MS ESI+: m/z=299 [M+H]+.

Methyl 2-(6-bromo-3-oxo-[1,2,4]triazolo[4,3-a]pyridin-2(3H)-yl)acetate

To a solution of 6-bromo-[1,2,4]triazolo[4,3-a]pyridin-3(2H)-one (5.5 g) in DMF (100 mL) was added K$_2$CO$_3$ (7.1 g) at RT. The suspension was stirred for 30 minutes and then added methyl 2-bromoacetate (5.9 g). The mixture was stirred for 20 hours at RT. The reaction mixture was partitioned between water (500 mL) and EA (100 mL×3). The combined organic phases were washed with water (50 mL×2) and brine (30 mL) and dried over Na$_2$SO$_4$. After filtration, the solvent was removed under reduced pressure and the residue was washed with n-hexane. The residue was dried under high vacuum to provide the title compound. MS ESI+: m/z=286 [M+H]+.

6-Bromo-2-methyl-[1,2,4]triazolo[4,3-a]pyridin-3(2H)-one

To a solution of 6-bromo-[1,2,4]triazolo[4,3-a]pyridin-3(2H)-one (3 g) in DMF (50 mL) was added K$_2$CO$_3$ (3.87 g) at RT. The suspension was stirred for 30 minutes and then added iodomethane (3.98 g). The mixture was stirred for 20 hours at RT The reaction mixture was partitioned between water (300 mL) and EA (100 mL×3). The organic phase was washed with brine and dried over Na$_2$SO$_4$. After filtration, the solvent was removed under reduced pressure to provide the title compound. MS ESI$^+$: m/z=228 [M+H]$^+$.

6-Bromo-[1,2,4]triazolo[4,3-a]pyridin-3(2H)-one

A suspension of 5-bromo-2-hydrazinylpyridine (6.0 g) and 1,1'-carbonyldiimidazole (5.69 g) in acetonitrile (75 mL) was heated under reflux for 2 hours. The reaction was cooled to RT. The precipitate was collected by filtration and washed with acetonitrile (25 mL) to provide the title compound. MS ESI$^+$: m/z=214 [M+H]$^+$.

5-Bromo-2-hydrazinylpyridine

Hydrazine monohydrate (10 mL) was added to a solution of 2,5-dibromopyridine (10 g) in pyridine (100 mL) at RT, and the mixture was heated under reflux for 16 hours. After cooling to RT, the volatiles were evaporated under reduced pressure. To the residue were added sodium hydroxide (100 mL, 0.5 N) and DCM (100 mL) and the phases were separated. The aqueous phase was extracted with DCM (100 mL×4). The combined organic layers were dried over anhydrous sodium sulfate. After filtration, the solvent was evaporated under reduced pressure to provide the subtitle compound. MS ESI$^+$: m/z=188 [M+H]$^+$.

2-(6-Bromo-8-fluoro-3-oxo-[1,2,4]triazolo[4,3-a] pyridin-2(3H)-yl)-N,N-dimethylacetamide To a mixture of 6-bromo-8-fluoro-[1,2,4]triazolo[4,3-a] pyridin-3(2H)-one (1.0 g) and DMF (10 mL) at 0° C. was added NaH (207 mg, 50% in mineral oil). After 20 minutes, 2-bromo-N,N-dimethyl-acetamide (716 mg) was added. The mixture was allowed to warm to RT and stirred for 2 hours. The mixture was poured into ammonium chloride (10% aqueous) and extracted with EA (3×). The combined organic layers were washed with brine, dried over dried over Na$_2$SO$_4$ and evaporated. The residue was slurried with MTBE and the resulting solid isolated by filtration to provide the title compound. MS ESI$^+$: m/z=317 [M+H]$^+$.

Methyl 2-(6-bromo-8-fluoro-3-oxo-[1,2,4]triazolo[4, 3-a]pyridin-2(3H)-yl)acetate To a suspension of 6-bromo-8-fluoro-[1,2,4]triazolo[4,3-a]pyridin-3(2H)-one (6.90 g) in DMF (70 mL) was added methyl 2-chloroacetate (6.48 g) and K$_2$CO$_3$ (8.24 g). After the addition, the resultant mixture was stirred at RT overnight. The reaction mixture was diluted with water (150 mL) and extracted with EA (100 mL×3). The combined organic layers were washed with water (50 mL×3), and brine (50 mL), dried over Na$_2$SO$_4$ and concentrated. The residue was purified by column chromatography on silica gel eluting with EA/DCM/PE (1:12:6) to provide the title compound. MS ESI$^+$: m/z=304 [M+H]$^+$.

6-Bromo-8-fluoro-2-methyl-[1,2,4]triazolo[4,3-a] pyridin-3(2H)-one

To a suspension of 6-bromo-8-fluoro-[1,2,4]triazolo[4,3-a]pyridin-3(2H)-one (3.0 g) in DMF (50 mL) was added MeI (1.62 mL) and K$_2$CO$_3$ (3.60 g). After the addition, the resultant mixture was stirred at RT overnight. The reaction mixture was diluted with water (150 mL) and extracted with EA (100 mL×3). The combined organic layers were washed with water (50 mL×3), and brine (50 mL), dried over Na$_2$SO$_4$ and concentrated. The residue was purified by column chromatography on silica gel eluting with EA/DCM/PE (1:12:6) to provide the title compound. MS ESI$^+$: m/z=246 [M+H]$^+$.

6-Bromo-8-fluoro-[1,2,4]triazolo[4,3-a]pyridin-3 (2H)-one

To a suspension of 5-bromo-3-fluoro-2-hydrazinylpyridine (53.25 mmol) in MeCN (100 mL) was added CDI (10.36 g). After the addition, the resultant mixture was stirred at 100° C. for 5 hours. The reaction mixture was concentrated. The residue was diluted with water (50 mL), crushed by ultrasound and filtered. The filter cake was dried in vacuo and recrystallized with DCM and MeOH to provide the title compound. MS ESI$^+$: m/z=232 [M+H]$^+$.

5-Bromo-3-fluoro-2-hydrazinylpyridine

To a solution of 5-bromo-2,3-difluoropyridine (12.0 g) in EtOH (100 mL) was added hydrazine hydrate (85%, 30 mL). After the addition, the resultant mixture was stirred at RT overnight. The reaction mixture was concentrated. The residue was diluted with water (50 mL), crushed by ultrasound and filtered. The filter cake was dried in vacuo to provide the subtitle compound. MS ESI$^+$: m/z=206 [M+H]$^+$.

Methyl 2-(6-bromo-2H-indazol-2-yl)acetate

To a mixture of 6-bromo-1H-indazole (2.5 g) and DMF (20 mL) was added NaH (716 mg, 50% in mineral oil). After 10 minutes, methyl bromoacetate (2.16 g) was added and the mixture stirred for 3 hours. The mixture was partitioned between water and ethyl acetate. The organic layer was dried over Na$_2$SO$_4$ and concentrated. The residue was purified by column chromatography on silica gel eluting with EA/heptane (2:1) to provide the title compound. MS ESI$^+$: m/z=269 [M+H]$^+$.

Methyl 2-(5-bromo-2H-benzo[d][1,2,3]triazol-2-yl)acetate

To a mixture of 2-(5-bromo-2H-benzo[d][1,2,3]triazol-2-yl)acetic acid (1.92 g) and methanol (90 mL) was added TMSCHN$_2$ (6.5 mL, 2 M in hexane). Evaporation of the mixture gave a residue which was separated by SGC (EA/heptane=1:2 to 1:1) to provide the title compound. MS ESI$^+$: m/z=270 [M+H]$^+$.

2-(5-Bromo-2H-benzo[d][1,2,3]triazol-2-yl)acetic acid

A mixture of NaOH (747 mg) and EtOH (20 mL) was heated until all NaOH was dissolved. At RT, 5-bromo-1H-benzotriazole (2.65 g) was added and the mixture heated to reflux. Sodium chloroacetate (2.22 g) was added portionwise. After 12 hours at reflux, the mixture was allowed to cool to RT and the precipitate was collected by filtration. The crude material was dissolved in water (50 mL) and the pH was adjusted to 3 by addition of conc. HCl. The resulting solid was isolated by filtration and washed with water to provide the subtitle compound (mixture of regioisomers). MS ESI$^+$: m/z=256 [M+H]$^+$. 2-(6-Bromo-4-fluoro-2H-benzo[d][1,2,3]triazol-2-yl)-N,N-dimethylacetamide A mixture of 5-bromo-7-fluoro-1H-benzo[d][1,2,3]triazole (1.98 g), cesium carbonate (5.97 g) and DMF (30 mL) was added 2-bromo-N,N-dimethyl-acetamide (1.60 g). After 2 days the mixture was filtrated and the volatiles were evaporated. The residue was separated by preparative HPLC to provide the title compound. MS ESI⁺: m/z=301 [M+H]⁺.

5-Bromo-7-fluoro-1H-benzo[d][1,2,3]triazole

A mixture of 5-bromo-3-fluorobenzene-1,2-diamine (650 mg), acetic acid (4.5 mL) and water (1.5 mL) was added at 0° C. HCl (0.2 mL, 35%) and NaNO₂ (280 mg in 1.5 mL water). After 30 minutes the mixture was partitioned between water and ethyl acetate. The aqueous phase was extracted twice with ethyl acetate. The combined organic layers were dried over Na₂SO₄ and concentrated to provide the subtitle compound. MS ESI⁺: m/z=216 [M+H]⁺.

Ethyl 2-(6-bromoimidazo[1,2-a]pyridin-2-yl)acetate

A mixture of neutral aluminum oxide (14.7 g), ethyl 4-bromoacetoacetate (3.02 g) and 2-amino-4-bromopyridine (2.5 g) was allowed to stand overnight. DCM (25 mL) was added and the mixture stirred for 24 hours. Insoluble material was removed by filtration over a short pad of silica gel eluting with DCM/MeOH. The filtrate was concentrated and purified by preparative HPLC to provide the title compound. MS ESI⁺: m/z=283 [M+H]⁺.

Preparation of Examples 2

Example 2-01 (Typical Procedure 7)

To a mixture of (R)-2-(6-(3-((6-(cyclopropylmethoxy)pyridin-3-yl)oxy)-2-oxopyrrolidin-1-yl)-8-fluoro-3-oxo-[1,2,4]triazolo[4,3-a]pyridin-2(3H)-yl)acetic acid (100 mg), DIPEA (85 mg) and DMF (2 mL) was added EDCl (46 mg) and HOBt (32 mg). After 30 minutes dimethylamine (120 µL, 2 M in THF) was added and the mixture stirred for 12 hours. Evaporation of the reaction mixture gave a residue which was purified by preparative HPLC to provide Example 2-01.

Following essentially this procedure the Examples 2 in Table 2 were obtained by coupling the appropriate acid with the respective amine.

TABLE 2

| Example | Structure | LCMS Method | R_t [min] | ESI⁺ m/z [amu] |
|---|---|---|---|---|
| 2-01 | 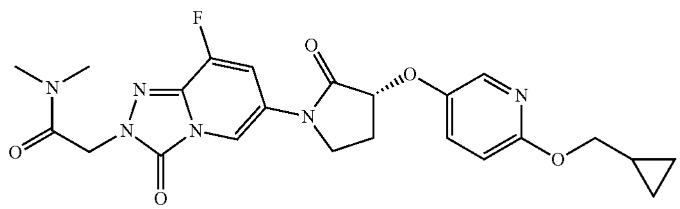 [SMILES: CN(C)C(=O)Cn1nc2c(F)cc(N3CC[C@@H](Oc4ccc(OCC5CC5)nc4)C3=O)cn2c1=O] | A | 1.68 | 485.4 |
| 2-02 | 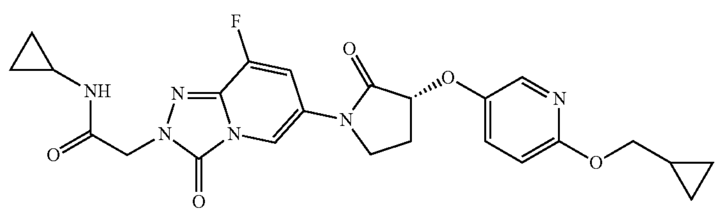 [SMILES: O=C(Cn1nc2c(F)cc(N3CC[C@@H](Oc4ccc(OCC5CC5)nc4)C3=O)cn2c1=O)NC1CC1] | A | 1.76 | 497.4 |
| 2-03 | 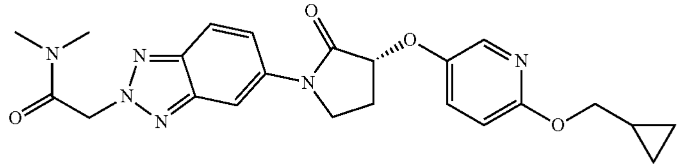 [SMILES: CN(C)C(=O)Cn1nc2ccc(N3CC[C@@H](Oc4ccc(OCC5CC5)nc4)C3=O)cc2n1] | A | 1.63 | 451.3 |
| 2-04 | 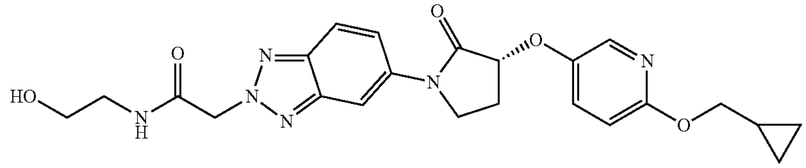 [SMILES: O=C(Cn1nc2ccc(N3CC[C@@H](Oc4ccc(OCC5CC5)nc4)C3=O)cc2n1)NCCO] | A | 1.53 | 467.3 |
| 2-05 | 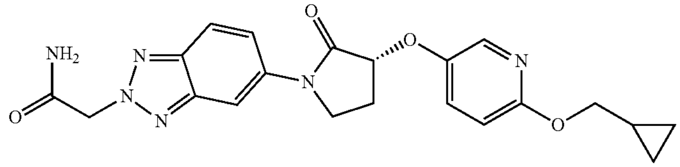 | A | 1.55 | 423.3 |

Pharmacological Utility

The biological activity of the compounds of the invention may be demonstrated by known in vitro assays. Examples include in vitro cellular assays for recombinant and non-recombinant GPR119 as described in the following.

Functional Cellular Assays Measuring GPR119-Mediated cAMP Release

Compounds of the invention, which are agonists of GPR119, were characterized by functional assays measuring the cAMP response of HEK-293 cell lines stably expressing recombinant GPR119 from man, mouse or rat, or by using a hamster cell line HIT-T15 expressing GPR119 endogenously. The cAMP content was determined using a kit based on homogenous time-resolved fluorescence (HTRF) from Cisbio Corp. (cat. no. 62AM4PEC). For preparation, cells were split into T175 culture flasks and grown to near confluency in medium (DMEM/10% FCS for HEK-293 cells, and F-12K medium/10% horse serum/2.5% FCS for HIT-T15 cells, respectively). Medium was then removed and cells washed with PBS lacking calcium and magnesium ions, followed by proteinase treatment with accutase (Sigma-Aldrich, cat. no. A6964). Detached cells were washed and resuspended in assay buffer (1×HBSS; 20 mM HEPES, 0.1% BSA, 2 mM IBMX) and cellular density determined. They were then diluted to 400000 cells/mL and 25 µL-aliquots dispensed to the wells of 96-well plates. For measurement, 25 µL of test compound in assay buffer was added and incubated for 30 minutes at room temperature. After addition of HTRF reagents diluted in lysis buffer, the plates were incubated for 1 hour, followed by measuring the fluorescence ratio at 665 vs. 620 nm. Potency of the agonists was quantified by determining the concentrations that caused 50% of the maximal response/activation ($EC_{50}$). See Table 3 for exemplary data obtained using the cell line expressing human GPR119.

Compounds of the invention show $EC_{50}$ values typically in the range of about 0.001 to 100 µM, preferably from about 0.001 to 10 µM, more preferably from about 0.001 to 1 µM and most preferably from about 0.001 to 0.3 µM.

TABLE 3

| Example | EC50 [µM] |
|---|---|
| 1-01 | 11.300 |
| 1-02 | 0.851 |
| 1-03 | 7.620 |
| 1-04 | 0.155 |
| 1-05 | 7.990 |
| 1-06 | 17.300 |
| 1-07 | 1.580 |
| 1-08 | 5.540 |
| 1-09 | 0.191 |
| 1-10 | 0.658 |
| 1-11 | 0.206 |
| 1-12 | 0.269 |
| 1-13 | 0.179 |
| 1-14 | 0.701 |
| 1-15 | 0.924 |
| 1-16 | 12.000 |
| 1-17 | 2.110 |
| 1-18 | 0.034 |
| 1-19 | >100 |
| 1-20 | 9.920 |
| 1-21 | 2.050 |
| 1-22 | 0.182 |
| 1-23 | 4.200 |
| 1-24 | 6.170 |
| 1-25 | 0.249 |
| 1-26 | 0.113 |
| 1-27 | 1.870 |
| 1-28 | 0.070 |
| 1-30 | 0.203 |
| 1-31 | 0.365 |
| 1-32 | 0.196 |
| 1-33 | 0.113 |
| 1-34 | 0.103 |
| 2-01 | 0.126 |
| 2-02 | 0.123 |
| 2-03 | 0.127 |
| 2-04 | 0.343 |
| 2-05 | 0.196 |
| empty | empty |

Based on the demonstrated ability of the compounds of the invention to activate GPR119 it is predicted that said compounds are useful for treatment of diseases and/or prevention of conditions which are modulated by GPR119.

Especially, the compounds of the invention may be useful to treat GPR119-related diseases and/or prevent GPR119-mediated conditions in humans.

The compounds of the invention are especially suitable for the treatment and/or prevention of:

1a) Disorders of fatty acid metabolism and glucose utilization disorders
1b) Disorders in which insulin resistance is involved
2) Diabetes mellitus, especially type 2 diabetes mellitus, including the prevention of the sequelae associated therewith. Particular aspects in this context are:
   a) Improvement of hyperglycemia
   b) Improvement of insulin resistance
   c) Improvement of glucose tolerance
   d) Protection of pancreatic beta cells
   e) Improvement of beta cell function
   f) Prevention of micro- and macrovascular disorders, such as
      a. Retinopathy
      b. Atherosclerosis
      c. Nephropathy and microalbuminuria
      d. Neuropathy
   g) Chronic low grade inflammation
3) Various other conditions which may be associated with the metabolic syndrome or the syndrome X, such as
   a) Increased abdominal girth
   b) Obesity
   c) Liver disorders
      a. Fatty liver
      b. Steatosis
      c. Steatohepatitis
      d. Cirrhosis
   d) Dyslipidemia (e.g. hypertriglyceridemia, hypercholesterolemia, hyperlipoproteinemia and/or low HDL)
   e) Insulin resistance
   f) Hypercoagulability
   g) Hyperuricemia
   h) Thromboses, hypercoagulable and prothrombotic states (arterial and venous)
   i) High blood pressure
   j) Endothelial dysfunction
   k) Heart failure, for example (but not limited to) following myocardial infarction, hypertensive heart disease or cardiomyopathy
4) Cardiovascular diseases, for example (but not limited to) myocardial infarction and stroke 5) Bone-related diseases and disorders characterized by reduced bone mass, such as:
   a) Osteoporosis
   b) Rheumatoid arthritis
   c) Osteoarthritis.

The invention claimed is:
1. A compound of formula I, a stereoisomeric form thereof, or a physiologically acceptable salt of any of the foregoing,

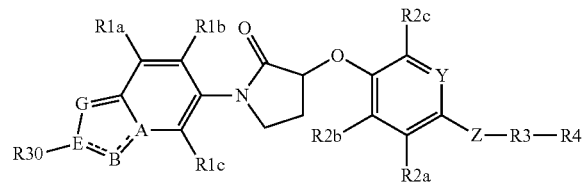

wherein
A is N or C;
B is CO, N or CH;
E is N or C;
G is N or CR30;
   wherein at least one of the groups A, B, E and G is N;
R30 is H or (CR11R12)$_n$-R32;
R11 and R12 are independently H or ($C_1$-$C_6$)-alkyl;
n is 0, 1, 2 or 3;
R32 is ($C_1$-$C_6$)-alkyl, ($C_3$-$C_8$)-cycloalkyl, COOR13, CONR14R15, SO$_2$R16 or OH;
R13 is H or ($C_1$-$C_6$)-alkyl;
R14 and R15 are independently H, ($C_1$-$C_6$)-alkyl, ($C_1$-$C_6$)-alkyl substituted with OR17, or ($C_3$-$C_6$)-cycloalkyl;
   or R14 and R15, together with the N-atom to which they are attached, form a 4-, 5- or 6-membered heterocycle, optionally containing an additional ring member selected from the group consisting of O, S and NR18;
      wherein the 4-, 5- or 6-membered heterocycle may be is optionally substituted with 1 to 3 groups selected from the group consisting of ($C_1$-$C_4$)-alkyl and OR17;
R16 is ($C_1$-$C_6$)-alkyl;
R17 is H or ($C_1$-$C_6$)-alkyl;
R18 is H or ($C_1$-$C_6$)-alkyl;
R1a, R1b, and R1c are independently H, F, Cl, Br, ($C_1$-$C_6$)-alkyl or CN;
R2a, R2b, and R2c are independently H, F, Cl, Br, ($C_1$-$C_6$)-alkyl or CN;
Y is N or CH;
Z is a bond, O, CR5R5', NR6, C=O, S, SO or SO$_2$;
R5, R5', and R6 are independently H or ($C_1$-$C_4$)-alkyl;
R3 is a bond or (CR7R7')$_p$;
p is 0, 1, 2, 3 or 4;
R7 and R7' are independently H or ($C_1$-$C_6$)-alkyl;
R4 is ($C_1$-$C_6$)-alkyl, OR8, ($C_3$-$C_8$)-cycloalkyl, ($C_5$-$C_8$)-bicycloalkyl, 4-, 5- or 6-membered heterocycle, phenyl or 5- or 6-membered heteroaryl ring;
   wherein the groups ($C_3$-$C_8$)-cycloalkyl, ($C_5$-$C_8$)-bicycloalkyl, 4-, 5- or 6-membered heterocycle, phenyl, 5- or 6-membered heteroaryl ring are optionally substituted with 1 to 3 groups selected from the group consisting of ($C_1$-$C_4$)-alkyl, ($C_1$-$C_4$)-alkanoyl, hydroxy, hydroxy-($C_1$-$C_4$)-alkyl, ($C_1$-$C_3$)-alkyloxy-($C_1$-$C_4$)-alkyl, oxo, F and Cl; and
R8 is H, ($C_1$-$C_6$)-alkyl, hydroxy-($C_1$-$C_4$)-alkyl or ($C_1$-$C_3$)-alkyloxy-($C_1$-$C_4$)-alkyl;
wherein at each occurrence a hydrogen atom of an alkyl group is optionally replaced by a fluorine atom.

2. The compound of claim 1, a stereoisomeric form thereof, or a physiologically acceptable salt of any of the foregoing, wherein the 3-position of the pyrrolidinone ring has (R)-configuration.

3. The compound of claim 1, a stereoisomeric form thereof, or a physiologically acceptable salt of any of the foregoing, wherein Y is N.

4. The compound of claim 1, a stereoisomeric form thereof, or a physiologically acceptable salt of any of the foregoing, wherein Z is O.

5. The compound of claim 1, a stereoisomeric form thereof, or a physiologically acceptable salt of any of the foregoing, wherein R3 is CH$_2$.

6. The compound of claim 1, a stereoisomeric form thereof, or a physiologically acceptable salt of any of the foregoing, wherein R4 is ($C_3$-$C_8$)-cycloalkyl.

7. The compound of claim 1, wherein the compound is of formula Ia, a stereoisomeric form thereof, or a physiologically acceptable salt of any of the foregoing,

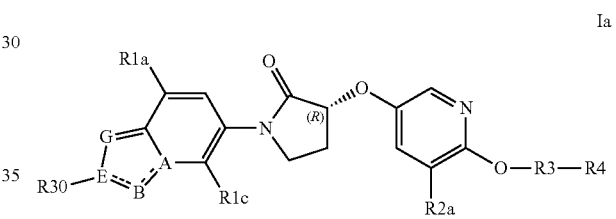

wherein
A is N or C;
B is CO, N or CH;
E is N or C;
G is N or CR30;
   wherein at least one of the groups A, B, E and G is N;
R30 is H or (CR11R12)$_n$-R32;
R11 and R12 are independently H or ($C_1$-$C_6$)-alkyl;
n is 0, 1, 2 or 3;
R32 is ($C_1$-$C_6$)-alkyl, ($C_3$-$C_8$)-cycloalkyl, COOR13, CONR14R15, SO$_2$R16 or OH;
R13 is H or ($C_1$-$C_6$)-alkyl;
R14 and R15 are independently H, ($C_1$-$C_6$)-alkyl, ($C_1$-$C_6$)-alkyl substituted with OR17, or ($C_3$-$C_6$)-cycloalkyl;
   or R14 and R15, together with the N-atom to which they are attached, form a 4-, 5- or 6-membered heterocycle, optionally containing an additional ring member selected from the group consisting of O, S and NR18;
      wherein the 4-, 5- or 6-membered heterocycle is optionally substituted with 1 to 3 groups selected from the group consisting of ($C_1$-$C_4$)-alkyl and OR17;
R16 is ($C_1$-$C_6$)-alkyl;
R17 is H or ($C_1$-$C_6$)-alkyl;
R18 is H or ($C_1$-$C_6$)-alkyl;
R1a and R1c are independently H, F, Cl, Br, ($C_1$-$C_6$)-alkyl or CN;

R2a is H, F, Cl, Br, $(C_1\text{-}C_6)$-alkyl or CN;
R3 is a bond or $(CR7R7')_p$;
p is 0, 1, 2, 3 or 4;
R7 and R7' are independently H or $(C_1\text{-}C_6)$-alkyl;
R4 is $(C_1\text{-}C_6)$-alkyl, OR8, $(C_3\text{-}C_8)$-cycloalkyl, $(C_5\text{-}C_8)$-bicycloalkyl, 4-, 5- or 6-membered heterocycle, phenyl or 5- or 6-membered heteroaryl ring;
wherein the groups $(C_3\text{-}C_8)$-cycloalkyl, $(C_5\text{-}C_8)$-bicycloalkyl, 4-, 5- or 6-membered heterocycle, phenyl, 5- or 6-membered heteroaryl ring are optionally substituted with 1 to 3 groups selected from the group consisting of $(C_1\text{-}C_4)$-alkyl, $(C_1\text{-}C_4)$-alkanoyl, hydroxy, hydroxy-$(C_1\text{-}C_4)$-alkyl, $(C_1\text{-}C_3)$-alkyloxy-$(C_1\text{-}C_4)$-alkyl, oxo, F and Cl; and
R8 is H, $(C_1\text{-}C_6)$-alkyl, hydroxy-$(C_1\text{-}C_4)$-alkyl or $(C_1\text{-}C_3)$-alkyloxy-$(C_1\text{-}C_4)$-alkyl;
wherein at each occurrence a hydrogen atom of an alkyl group is optionally replaced by a fluorine atom.

8. The compound of claim 7, a stereoisomeric form thereof, or a physiologically acceptable salt of any of the foregoing, wherein
R30 is $(CR11R12)_n\text{-}R32$;
n is 0, 1 or 2;
R32 is $(C_1\text{-}C_6)$-alkyl, $(C_3\text{-}C_8)$-cycloalkyl, COOR13, CONR14R15 or OH;
R3 is $CH_2$; and
R4 is $(C_3\text{-}C_8)$-cycloalkyl which may be optionally substituted with 1 to 3 groups selected from the group consisting of $(C_1\text{-}C_4)$-alkyl and F;
wherein at each occurrence a hydrogen atom of an alkyl group is optionally replaced by a fluorine atom.

9. The compound of claim 7, a stereoisomeric form thereof, or a physiologically acceptable salt of any of the foregoing, wherein
R30 is $(CR11R12)_n\text{-}R32$;
n is 0, 1 or 2;
R32 is $(C_1\text{-}C_6)$-alkyl, $(C_3\text{-}C_8)$-cycloalkyl, COOR13, CONR14R15 or OH;
R3 is $CH_2$; and
R4 $(C_3\text{-}C_8)$-cycloalkyl;
wherein at each occurrence a hydrogen atom of an alkyl group is optionally replaced by a fluorine atom.

10. The compound of claim 7, a stereoisomeric form thereof, or a physiologically acceptable salt of any of the foregoing, wherein
R30 is $CH_2CONR14R15$;
R1a and R1c are independently H or F;
R2a is H;
R3 is $CH_2$; and
R4 is $(C_3\text{-}C_8)$-cycloalkyl.

11. A compound selected from the group consisting of:
(3R)-3-[[6-(Cyclopropylmethoxy)-3-pyridyl]oxy]-1-(2-cyclopropyl-[1,2,4]triazolo[1,5-a]pyridin-6-yl)pyrrolidin-2-one;
(3R)-3-[[6-(cyclopropylmethoxy)-3-pyridyl]oxy]-1-([1,2,4]triazolo[1,5-a]pyridin-6-yl)pyrrolidin-2-one;
(3R)-3-[[6-(cyclopropylmethoxy)-3-pyridyl]oxy]-1-imidazo[1,2-a]pyridin-6-yl-pyrrolidin-2-one;
methyl 2-[6-[(3R)-3-[[6-(cyclopropylmethoxy)-3-pyridyl]oxy]-2-oxo-pyrrolidin-1-yl]-1-methyl-3-oxo-imidazo[1,5-a]pyridin-2-yl]acetate;
(3R)-3-[[6-(cyclopropylmethoxy)-3-pyridyl]oxy]-1-([1,2,4]triazolo[4,3-a]pyridin-6-yl)pyrrolidin-2-one;
2-[6-[(3R)-3-[[6-(cyclopropylmethoxy)-3-pyridyl]oxy]-2-oxo-pyrrolidin-1-yl]-[1,2,4]triazolo[1,5-a]pyridin-2-yl]acetic acid;
methyl 2-[6-[(3R)-3-[[6-(cyclopropylmethoxy)-3-pyridyl]oxy]-2-oxo-pyrrolidin-1-yl]-[1,2,4]triazolo[1,5-a]pyridin-2-yl]acetate;
methyl 6-[(3R)-3-[[6-(cyclopropylmethoxy)-3-pyridyl]oxy]-2-oxo-pyrrolidin-1-yl]-[1,2,4]triazolo[1,5-a]pyridine-2-carboxylate;
2-[6-[(3R)-3-[[6-(cyclopropylmethoxy)-3-pyridyl]oxy]-2-oxo-pyrrolidin-1-yl]-3-oxo-[1,2,4]triazolo[4,3-a]pyridin-2-yl]-N,N-dimethyl-acetamide;
8-fluoro-6-[(3R)-3-[[6-(4-fluorophenoxy)-3-pyridyl]oxy]-2-oxo-pyrrolidin-1-yl]-2H-[1,2,4]triazolo[4,3-a]pyridin-3-one;
2-[6-[(3R)-3-[[6-(4-fluorophenoxy)-3-pyridyl]oxy]-2-oxo-pyrrolidin-1-yl]-3-oxo-[1,2,4]triazolo[4,3-a]pyridin-2-yl]-N,N-dimethyl-acetamide;
2-[6-[(3R)-3-[4-(2-cyclopropylacetyl)phenoxy]-2-oxo-pyrrolidin-1-yl]-3-oxo-[1,2,4]triazolo[4,3-a]pyridin-2-yl]-N,N-dimethyl-acetamide;
2-[6-[(3R)-3-[4-(2-cyclopropylacetyl)phenoxy]-2-oxo-pyrrolidin-1-yl]-8-fluoro-3-oxo-[1,2,4]triazolo[4,3-a]pyridin-2-yl]-N,N-dimethyl-acetamide;
6-[(3R)-3-[[6-(cyclopropylmethoxy)-3-pyridyl]oxy]-2-oxo-pyrrolidin-1-yl]-2H-[1,2,4]triazolo[4,3-a]pyridin-3-one;
methyl 2-[6-[(3R)-3-[[6-(cyclopropylmethoxy)-3-pyridyl]oxy]-2-oxo-pyrrolidin-1-yl]indazol-2-yl]acetate;
2-[6-[(3R)-3-[[6-(cyclopropylmethoxy)-3-pyridyl]oxy]-2-oxo-pyrrolidin-1-yl]indazol-2-yl]acetic acid;
2-[5-[(3R)-3-[[6-(cyclopropylmethoxy)-3-pyridyl]oxy]-2-oxo-pyrrolidin-1-yl]benzotriazol-2-yl]acetic acid;
methyl 2-[5-[(3R)-3-[[6-(cyclopropylmethoxy)-3-pyridyl]oxy]-2-oxo-pyrrolidin-1-yl]benzotriazol-2-yl]acetate;
2-[6-[(3R)-3-[[6-(cyclopropylmethoxy)-3-pyridyl]oxy]-2-oxo-pyrrolidin-1-yl]imidazo[1,2-a]pyridin-2-yl]acetic acid;
methyl 2-[6-[(3R)-3-[[6-(cyclopropylmethoxy)-3-pyridyl]oxy]-2-oxo-pyrrolidin-1-yl]imidazo[1,2-a]pyridin-2-yl]acetate;
(3R)-3-[[6-(cyclopropylmethoxy)-3-pyridyl]oxy]-1-(2-methylbenzotriazol-5-yl)pyrrolidin-2-one;
2-[6-[(3R)-3-[[6-(cyclopropylmethoxy)-3-pyridyl]oxy]-2-oxo-pyrrolidin-1-yl]-4-fluorobenzotriazol-2-yl]-N,N-dimethyl-acetamide;
6-[(3R)-3-[[6-(cyclopropylmethoxy)-3-pyridyl]oxy]-2-oxo-pyrrolidin-1-yl]-2-methyl-[1,2,4]triazolo[4,3-a]pyridin-3-one;
2-[6-[(3R)-3-[[6-(cyclopropylmethoxy)-3-pyridyl]oxy]-2-oxo-pyrrolidin-1-yl]-3-oxo-[1,2,4]triazolo[4,3-a]pyridin-2-yl]acetic acid;
6-[(3R)-3-[[6-(cyclopropylmethoxy)-3-pyridyl]oxy]-2-oxo-pyrrolidin-1-yl]-8-fluoro-2H-[1,2,4]triazolo[4,3-a]pyridin-3-one;
methyl 2-[6-[(3R)-3-[[6-(cyclopropylmethoxy)-3-pyridyl]oxy]-2-oxo-pyrrolidin-1-yl]-3-oxo-[1,2,4]triazolo[4,3-a]pyridin-2-yl]acetate;
6-[(3R)-3-[[6-(cyclopropylmethoxy)-3-pyridyl]oxy]-2-oxo-pyrrolidin-1-yl]-8-fluoro-2-methyl-[1,2,4]triazolo[4,3-a]pyridin-3-one;
methyl 2-[6-[(3R)-3-[[6-(cyclopropylmethoxy)-3-pyridyl]oxy]-2-oxo-pyrrolidin-1-yl]-8-fluoro-3-oxo-[1,2,4]triazolo[4,3-a]pyridin-2-yl]acetate;
(R)-2-(6-(3-((6-(cyclopropylmethoxy)pyridin-3-yl)oxy)-2-oxopyrrolidin-1-yl)-8-fluoro-3-oxo-[1,2,4]triazolo[4,3-a]pyridin-2(3H)-yl)acetic acid;

2-[6-[(3R)-3-[[6-(cyclopropylmethoxy)-3-pyridyl]oxy]-2-oxo-pyrrolidin-1-yl]-8-fluoro-3-oxo-[1,2,4]triazolo[4,3-a]pyridin-2-yl]-N,N-dimethyl-acetamide;

N-cyclopropyl-2-[6-[(3R)-3-[[6-(cyclopropylmethoxy)-3-pyridyl]oxy]-2-oxo-pyrrolidin-1-yl]-8-fluoro-3-oxo-[1,2,4]triazolo[4,3-a]pyridin-2-yl]acetamide;

2-[5-[(3R)-3-[[6-(cyclopropylmethoxy)-3-pyridyl]oxy]-2-oxo-pyrrolidin-1-yl]benzotriazol-2-yl]-N,N-dimethyl-acetamide;

2-[5-[(3R)-3-[[6-(cyclopropylmethoxy)-3-pyridyl]oxy]-2-oxo-pyrrolidin-1-yl]benzotriazol-2-yl]-N-(2-hydroxyethyl)acetamide;

2-[5-[(3R)-3-[[6-(cyclopropylmethoxy)-3-pyridyl]oxy]-2-oxo-pyrrolidin-1-yl]benzotriazol-2-yl]acetamide; and N,N-dimethyl-2-[3-oxo-6-[(3R)-2-oxo-3-[[6-(2,2,2-trifluoroethoxy)-3-pyridyl]oxy]pyrrolidin-1-yl]-[1,2,4]triazolo[4,3-a]pyridin-2-yl]acetamide, or a pharmaceutically acceptable salt thereof.

12. The compound of claim 11, wherein the compound is 2-[6-[(3R)-3-[[6-(4-fluorophenoxy)-3-pyridyl]oxy]-2-oxo-pyrrolidin-1-yl]-3-oxo-[1,2,4]triazolo[4,3-a]pyridin-2-yl]-N,N-dimethyl-acetamide, or a pharmaceutically acceptable salt thereof.

13. The compound of claim 11, wherein the compound is 2-[6-[(3R)-3-[[6-(cyclopropylmethoxy)-3-pyridyl]oxy]-2-oxo-pyrrolidin-1-yl]-8-fluoro-3-oxo-[1,2,4]triazolo[4,3-a]pyridin-2-yl]-N,N-dimethyl-acetamide, or a pharmaceutically acceptable salt thereof.

14. The compound of claim 11, wherein the compound is N-cyclopropyl-2-[6-[(3R)-3-[[6-(cyclopropylmethoxy)-3-pyridyl]oxy]-2-oxo-pyrrolidin-1-yl]-8-fluoro-3-oxo-[1,2,4]triazolo[4,3-a]pyridin-2-yl]acetamide, or a pharmaceutically acceptable salt thereof.

15. A pharmaceutical composition comprising at least one compound of claim 1, or a physiologically acceptable salt thereof, and a pharmaceutically acceptable carrier.

16. The pharmaceutical composition of claim 15, further comprising one or more active ingredients selected from the group consisting of:

Insulin and insulin derivatives; GLP-1, GLP-1 analogues and GLP-1 receptor agonists; polymer bound GLP-1 and GLP-1 analogues; dual GLP-1/GIP agonists; dual GLP-1/glucagon receptor agonists; PYY3-36 or analogues thereof; pancreatic polypeptide or analogues thereof; glucagon receptor agonists or antagonists; GIP receptor agonists or antagonists; ghrelin antagonists or inverse agonists; xenin and analogues thereof; DDP-IV inhibitors; SGLT-2 inhibitors; dual SGLT-2/SGLT-1 inhibitors; biguanides; thiazolidinediones; PPAR agonists; PPAR modulators; sulfonylureas; meglitinides; alpha-glucosidase inhibitors; amylin and amylin analogues; GPR119 agonists; GPR40 agonists; GPR120 agonists; GPR142 agonists; TGR5 agonists; AMPK stimulants; AMPK activators; inhibitors of 11-beta-HSD; activators of glucokinase; inhibitors of DGAT; inhibitors of protein tyrosine phosphatase 1; inhibitors of glucose-6-phosphatase; inhibitors of fructose-1,6-bisphosphatase; inhibitors of glycogen phosphorylase; inhibitors of phosphoenol pyruvate carboxykinase; inhibitors of glycogen synthase kinase; inhibitors of pyruvate dehydrogenase kinase; CCR-2 antagonists; modulators of glucose transporter-4; somatostatin receptor 3 agonists; HMG-CoA-reductase inhibitors; fibrates; nicotinic acid and derivatives thereof; nicotinic acid receptor 1 agonists; ACAT inhibitors; cholesterol absorption inhibitors; bile acid-binding substances; IBAT inhibitors; MTP inhibitors; modulators of PCSK9; LDL receptor up-regulators (liver selective thyroid hormone receptor beta agonists); HDL-raising compounds; lipid metabolism modulators; PLA2 inhibitors; ApoA-I enhancers; cholesterol synthesis inhibitors; omega-3 fatty acids and derivatives thereof; active substances for the treatment of obesity; CB1 receptor antagonists; MCH-1 antagonists; MC4 receptor agonists and partial agonists; NPY5 or NPY2 antagonists; NPY4 agonists; beta-3 adrenergic receptor agonists; leptin or leptin mimetics; 5HT2c receptor agonists; lipase inhibitors; angiogenesis inhibitors; H3 antagonists; AgRP inhibitors; triple monoamine uptake inhibitors; MetAP2 inhibitors; antisense oligonucleotides against production of fibroblast growth factor receptor 4 or prohibitin targeting peptide-1; drugs for influencing high blood pressure; chronic heart failure or atherosclerosis; angiotensin II receptor antagonists; dual angiotensin receptor blockers (ARB); angiotensin converting enzyme (ACE) inhibitors; angiotensin converting enzyme 2 (ACE-2) activators; renin inhibitors; prorenin inhibitors; endothelin converting enzyme (ECE) inhibitors; endothelin receptor blockers; endothelin antagonists; diuretics; aldosterone antagonists; aldosterone synthase inhibitors; alpha-blockers; antagonists of the alpha-2 adrenergic receptor; beta-blockers; mixed alpha-/beta-blockers; calcium antagonists/calcium channel blockers (CBBs); dual mineralocorticoid/CCBs; centrally acting antihypertensives; inhibitors of neutral endopeptidase; aminopeptidase-A inhibitors; vasopeptide inhibitors; dual vasopeptide inhibitors; neprilysin-ACE inhibitors; neprilysin-ECE inhibitors; dual-acting Angiotensin (AT) receptor-neprilysin inhibitors; dual AT1/endothelin-1 (ETA) antagonists; advanced glycation end-product breakers; recombinant renalase; blood pressure vaccines; anti-RAAS vaccines; AT1- or AT2-vaccines; modulators of genetic polymorphisms with antihypertensive response; and thrombocyte aggregation inhibitors.

17. The pharmaceutical composition of claim 15, further comprising metformin.

18. The pharmaceutical composition of claim 15, further comprising at least one DPP-IV inhibitor.

19. The pharmaceutical composition of claim 18, wherein the at least one DPP-IV inhibitor is selected from the group consisting of alogliptin, linagliptin, saxagliptin, sitagliptin, anagliptin, teneligliptin, trelagliptin, vildagliptin, gemigliptin, omarigliptin, evogliptin and dutogliptin.

20. The pharmaceutical composition of claim 15, further comprising at least one SGLT-2 inhibitor.

21. The pharmaceutical composition of claim 20, wherein the at least one SGLT-2 inhibitor is selected from the group consisting of canagliflozin, dapagliflozin, remogliflozin, remogliflozin etabonate, sergliflozin, empagliflozin, ipragliflozin, tofogliflozin, luseogliflozin and ertugliflozin.

22. The pharmaceutical composition of claim 15, further comprising at least one GPR40 agonist.

23. The pharmaceutical composition of claim 22, wherein the at least one GPR40 agonist is selected from the group consisting of TUG-424, P-1736, P-11187, JTT-851, GW9508, CNX-011-67, AM-1638 and AM-5262.

24. The pharmaceutical composition of claim 15, further comprising ezetimibe.

25. The pharmaceutical composition of claim 15, further comprising at least one HMG-CoA reductase inhibitor.

26. The pharmaceutical composition of claim 25, wherein the at least one HMG-CoA reductase inhibitor is selected from the group consisting of simvastatin, atorvastatin, rosuvastatin, pravastatin, fluvastatin, pitavastatin, lovastatin, mevastatin, rivastatin and cerivastatin.

27. The pharmaceutical composition of claim 15, further comprising at least one PPAR agonist or PPAR modulator.

28. The pharmaceutical composition of claim 27, wherein the at least one PPAR agonist or PPAR modulator is saroglitazar.

29. The pharmaceutical composition of claim 27, wherein the at least one PPAR agonist or PPAR modulator is selected from the group consisting of pioglitazone, rosiglitazone and lobeglitazone.

30. The pharmaceutical composition of claim 15, further comprising acarbose.

31. A compound selected from the group consisting of:
6-[(3R)-3-[[6-(4-fluorophenoxy)-3-pyridyl]oxy]-2-oxopyrrolidin-1-yl]-2-(methylsulfonylmethyl)-[1,2,4]triazolo[4,3-a]pyridin-3-one;
6-[(3R)-3-[4-(cyclopropanecarbonyl)phenoxy]-2-oxopyrrolidin-1-yl]-2-(methylsulfonylmethyl)-[1,2,4]triazolo[4,3-a]pyridin-3-one;
2-(methylsulfonylmethyl)-6-[(3R)-2-oxo-3-[[6-(2,2,2-trifluoroethoxy)-3-pyridyl]oxy]pyrrolidin-1-yl]-[1,2,4]triazolo[4,3-a]pyridin-3-one; and
N,N-dimethyl-2-[5-[(3R)-2-oxo-3-[[6-(2,2,2-trifluoroethoxy)-3-pyridyl]oxy]pyrrolidin-1-yl]indazol-2-yl]acetamide,
or a pharmaceutically acceptable salt thereof.

* * * * *